US011536818B2

(12) United States Patent
Yang et al.

(10) Patent No.: US 11,536,818 B2
(45) Date of Patent: Dec. 27, 2022

(54) METHODS AND APPARATUSES FOR PROCESSING ULTRASOUND SIGNALS

(71) Applicant: BFLY OPERATIONS, INC., Burlington, MA (US)

(72) Inventors: Jungwook Yang, Burlington, MA (US); Daniel Rea McMahill, Woodstock, GA (US); Kailiang Chen, Branford, CT (US); Nevada J. Sanchez, Guilford, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 155 days.

(21) Appl. No.: 16/910,897

(22) Filed: Jun. 24, 2020

(65) Prior Publication Data

US 2020/0405267 A1   Dec. 31, 2020

Related U.S. Application Data

(60) Provisional application No. 62/866,221, filed on Jun. 25, 2019.

(51) Int. Cl.
*H03M 7/16* (2006.01)
*G01S 7/52* (2006.01)
(Continued)

(52) U.S. Cl.
CPC ........... *G01S 7/52025* (2013.01); *H03M 7/16* (2013.01); *A61B 8/4236* (2013.01); *A61B 8/5207* (2013.01)

(58) Field of Classification Search
CPC ...... H03M 7/16; A61B 8/4236; A61B 8/5207; G01S 7/52025; G01S 7/5202; G01S 7/52079
(Continued)

(56) References Cited

U.S. PATENT DOCUMENTS 6,078,276 A   6/2000  Signell et al.
9,229,097 B2  1/2016  Rothberg et al.
(Continued)

FOREIGN PATENT DOCUMENTS

WO   WO 2017/222964 A1   12/2017
WO   WO 2018/052702 A1   3/2018
WO   WO 2019/099638 A1   5/2019

OTHER PUBLICATIONS

International Search Report and Written Opinion dated Oct. 30, 2020 in connection with International Application No. PCT/US2020/039349.
(Continued)

*Primary Examiner* — Lam T Mai
(74) *Attorney, Agent, or Firm* — Osha Bergman Watanabe & Burton LLP

(57) ABSTRACT

Aspects of the technology described herein related to an ultrasound processing unit (UPU) including gray-coding circuitry configured to convert standard binary-coded digital ultrasound signals to gray-coded digital ultrasound signals and gray-decoding circuitry coupled to the gray-coding circuitry and configured to convert the gray-coded digital ultrasound signals to standard binary-coded digital ultrasound signals. The UPU may include an analog portion, a digital portion, and a data bus configured to route the gray-coded digital ultrasound signals from the analog portion to the digital portion subsequent to converting the standard binary-coded digital ultrasound signals to the gray-coded digital ultrasound signals. The analog portion may include multiple analog front-ends (AFEs), the gray-coding circuitry, and an analog-to-digital converter. The digital portion may include the gray-decoding circuitry. A data bus from one AFE may pass over another AFE.

16 Claims, 16 Drawing Sheets

(51) Int. Cl.
*A61B 8/08* (2006.01)
*A61B 8/00* (2006.01)

(58) Field of Classification Search
USPC .......................................................... 382/237
See application file for complete search history.

(56) References Cited

U.S. PATENT DOCUMENTS

| | | |
|---|---|---|
| 9,473,136 B1 | 10/2016 | Chen et al. |
| 9,521,991 B2 | 12/2016 | Rothberg et al. |
| 9,592,030 B2 | 3/2017 | Rothberg et al. |
| 9,933,516 B2 | 4/2018 | Chen et al. |
| 10,014,871 B2 | 7/2018 | Chen et al. |
| 10,702,242 B2 | 7/2020 | de Jonge et al. |
| 10,709,415 B2 | 7/2020 | Neben et al. |
| 11,129,595 B2 * | 9/2021 | Hagihara ............ G01S 7/52028 |
| 2010/0305449 A1 | 12/2010 | Wegener et al. |
| 2011/0012662 A1 | 1/2011 | Ma et al. |
| 2011/0055447 A1 | 3/2011 | Costa |
| 2013/0253325 A1 | 9/2013 | Call et al. |
| 2013/0278451 A1 | 10/2013 | Kim et al. |
| 2014/0107486 A1 | 4/2014 | Kaplan et al. |
| 2016/0120512 A1 * | 5/2016 | Hagihara ............ G01S 15/8915 600/443 |
| 2017/0360397 A1 | 12/2017 | Rothberg et al. |
| 2017/0360399 A1 | 12/2017 | Rothberg et al. |
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2017/0360404 A1 | 12/2017 | Gafner et al. |
| 2017/0360411 A1 | 12/2017 | Rothberg et al. |
| 2017/0360412 A1 | 12/2017 | Rothberg et al. |
| 2018/0325490 A1 | 11/2018 | Ku et al. |
| 2018/0364200 A1 | 12/2018 | Chen et al. |
| 2018/0366102 A1 | 12/2018 | Ralston et al. |
| 2019/0142388 A1 | 5/2019 | Gonyeau et al. |
| 2019/0307428 A1 | 10/2019 | Silberman et al. |
| 2020/0046314 A1 | 2/2020 | Neben et al. |
| 2020/0129151 A1 | 4/2020 | Neben et al. |
| 2020/0155113 A1 | 5/2020 | Neben et al. |
| 2020/0405266 A1 * | 12/2020 | Yang ...................... A61B 8/488 |
| 2021/0310996 A1 * | 10/2021 | Jain ........................ G01N 29/36 |

OTHER PUBLICATIONS

Hamlin, A Low Power Mid-Rail Dual Slope Analog-To-Digital Converter for Biomedical Instrumentation. Masters Thesis, University of Tennessee. Trace: Tennessee Research and Creative Exchange. May 2018; 50 pages.

Kester, Data Converter Codes—Can You Decode Them? MT-009 Tutorial. Analog Devices. 2009; 11 pages.

PCT/US2020/039349, Oct. 30, 2020, International Search Report and Written Opinion.

International Preliminary Report on Patentability for International Application No. PCT/US2020/039349, dated Jan. 6, 2022.

* cited by examiner

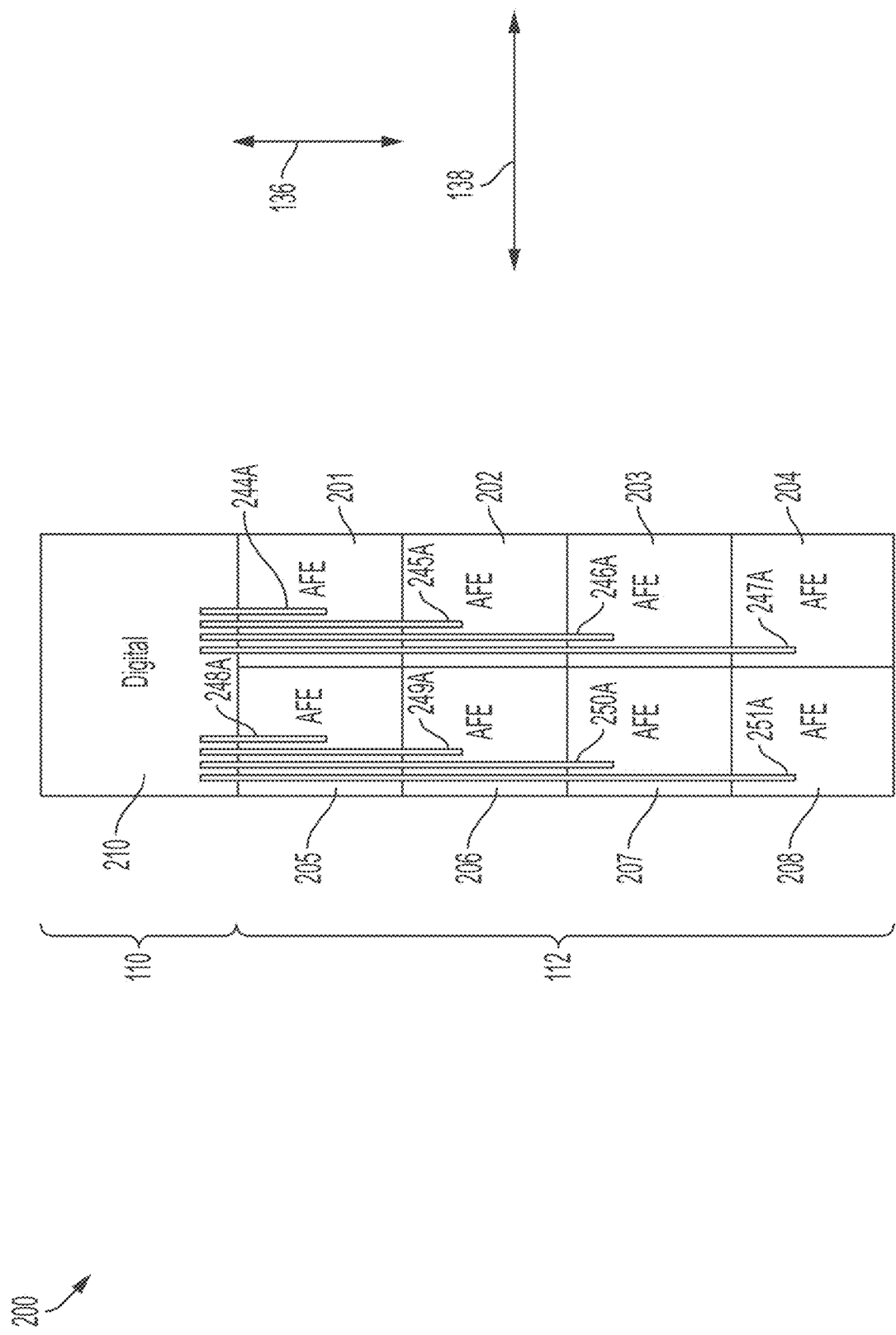

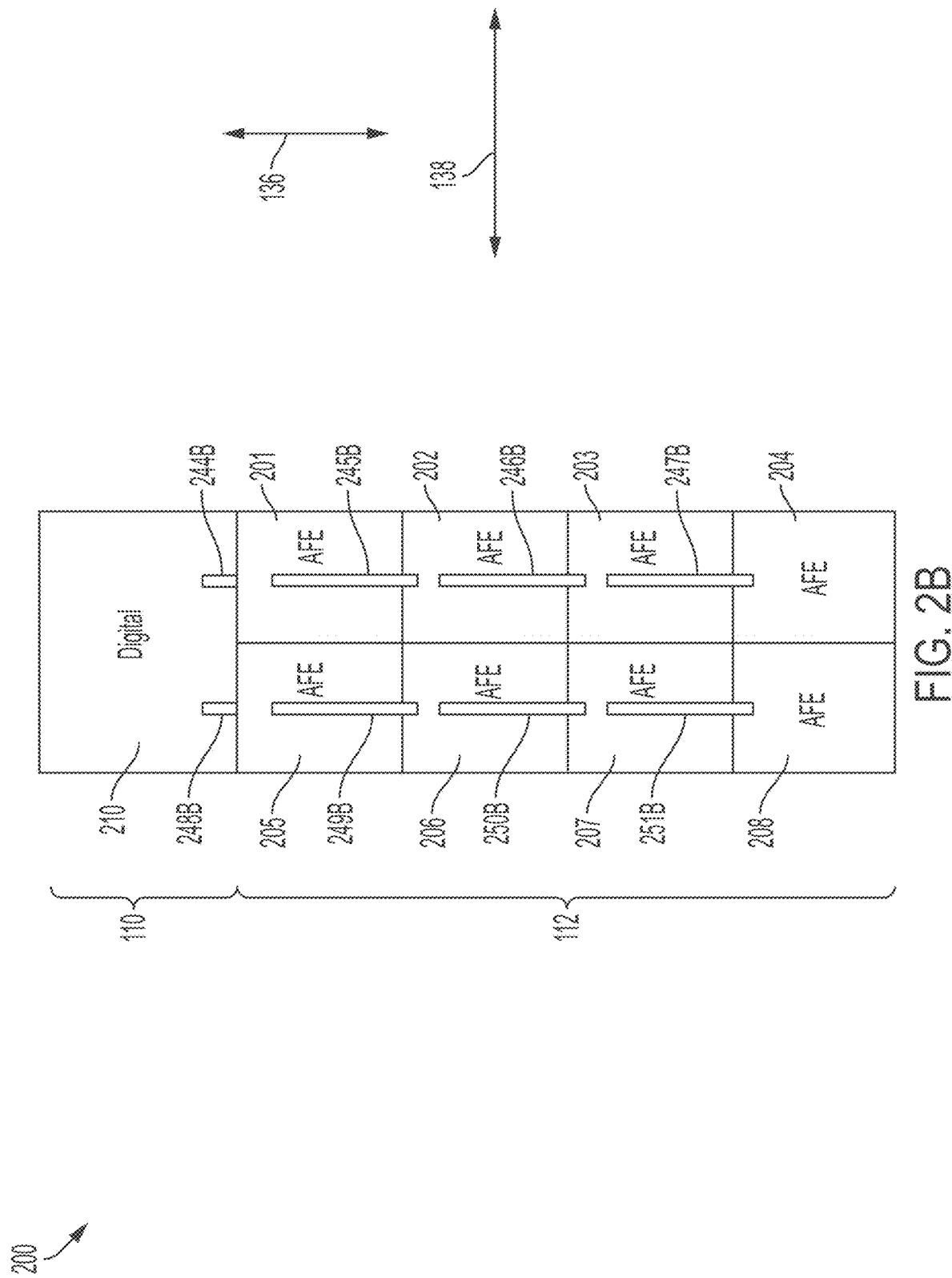

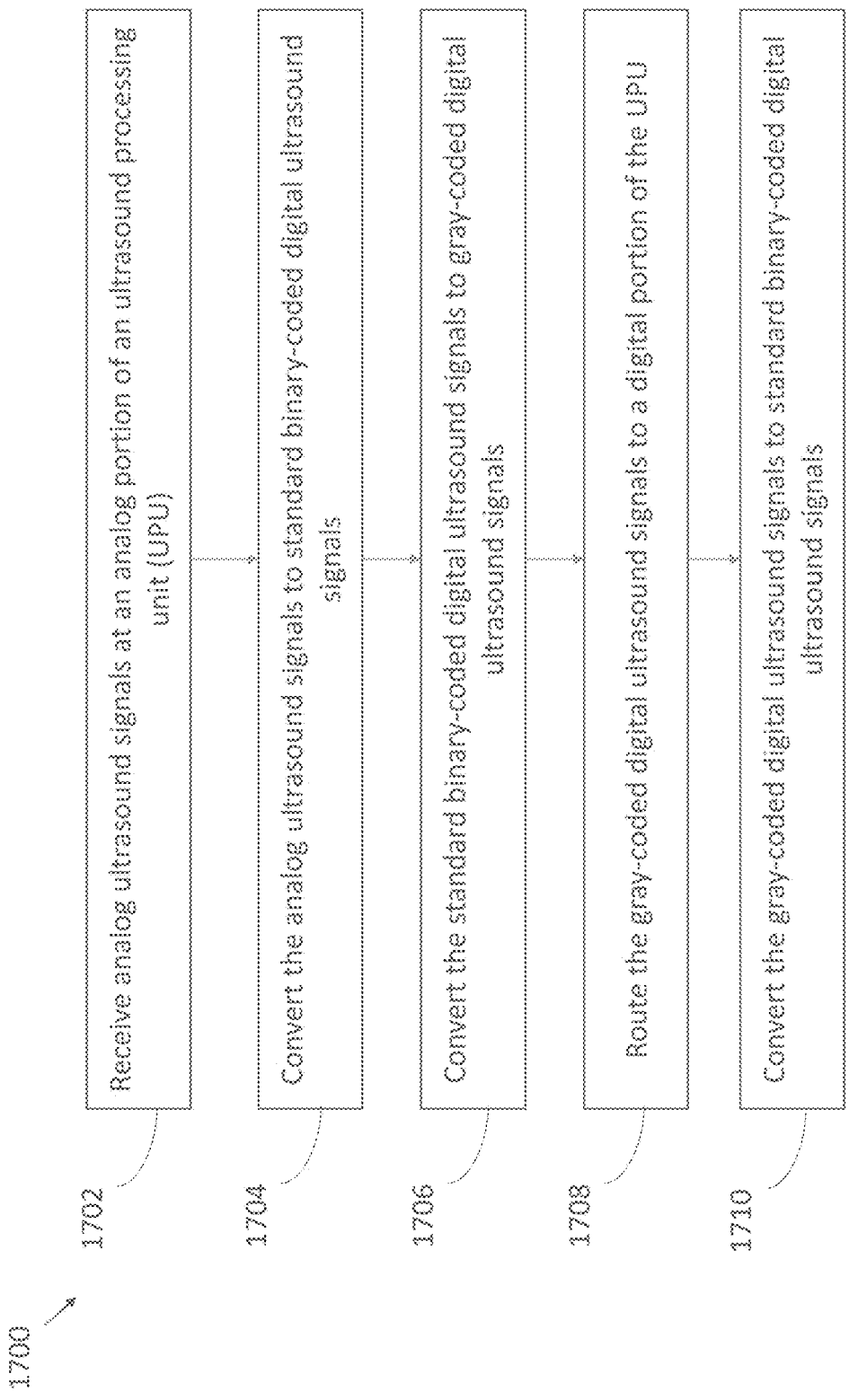

METHODS AND APPARATUSES FOR PROCESSING ULTRASOUND SIGNALS

CROSS-REFERENCE TO RELATED APPLICATIONS

This application claims the benefit under 35 U.S.C. § 119(e) of U.S. Patent Application Ser. No. 62/866,221, filed Jun. 25, 2019 under Attorney Docket No. B1348.70147US00 and entitled "METHODS AND APPARATUSES FOR PROCESSING ULTRASOUND SIGNALS," which is hereby incorporated by reference herein in its entirety.

FIELD

Generally, the aspects of the technology described herein relate to processing ultrasound signals. Some aspects relate to methods and apparatuses for gray coding and decoding digital ultrasound signals.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, an ultrasound processing unit (UPU) includes gray-coding circuitry configured to convert standard binary-coded digital ultrasound signals to gray-coded digital ultrasound signals.

In some embodiments, the UPU further includes gray-decoding circuitry coupled to the gray-coding circuitry and configured to convert the gray-coded digital ultrasound signals to standard binary-coded digital ultrasound signals. In some embodiments, the UPU further includes a digital portion including the gray-decoding circuitry, and a data bus coupled between the gray-coding circuitry and the gray-decoding circuitry and configured to route the gray-coded digital ultrasound signals to the digital portion subsequent to converting, by the gray-coding circuitry, the standard binary-coded digital ultrasound signals to the gray-coded digital ultrasound signals. In some embodiments, the digital portion includes digital processing circuitry.

In some embodiments, the UPU further includes an analog portion configured to receive analog ultrasound signals, the analog portion including an analog-to-digital converter (ADC) coupled to the gray-coding circuitry and configured to convert the analog ultrasound signals to the standard binary-coded digital ultrasound signals prior to converting, by the gray-coding circuitry, the standard binary-coded digital ultrasound signals to the gray-coded digital ultrasound signals; and the gray-coding circuitry. In some embodiments, the UPU further includes an analog portion configured to receive analog ultrasound signals, the analog portion including: multiple analog front-ends (AFEs), a first AFE of the multiple AFEs including: the gray-coding circuitry; and an analog-to-digital converter (ADC) coupled to the gray-coding circuitry and configured to convert the analog ultrasound signals to the standard binary-coded digital ultrasound signals prior to converting, by the gray-coding circuitry, the standard binary-coded digital ultrasound signals to the gray-coded digital ultrasound signals; wherein the data bus passes over a second AFE of the multiple AFEs. In some embodiments, the UPU further includes multiple data buses each coupled between one of the multiple AFEs and the digital portion. In some embodiments, the analog portion and the digital portion are physically separated.

In some embodiments, the analog portion further includes a pulser, a switch, and analog processing circuitry. In some embodiments, an ultrasound-on-chip includes the ultrasound processing unit, and the multiple AFEs are arranged along an elevational dimension of the ultrasound-on-chip. In some embodiments, ultrasonic transducers physically located on top of each of the AFEs and arranged along the elevational dimension of the ultrasound-on-chip. In some embodiments, the ultrasound-on-chip includes an array of ultrasonic transducers along an azimuthal dimension and an elevational dimension of the ultrasound-on-chip.

In some embodiments, the gray-coding circuitry is configured to convert the standard binary-coded digital ultrasound signals to full gray-coded digital ultrasound signals. In some embodiments, the gray-coding circuitry is configured to convert the standard binary-coded digital ultrasound signals to the full gray-coded digital ultrasound signals such that every transition from one binary code to an adjacent binary code differs by only a single bit. In some embodiments, the gray-coding circuitry is configured to convert a standard binary coded value $b_{N-1}b_{N-2} \ldots b_1b_0$ to a gray coded value $g_{N-1}g_{N-2} \ldots g_1g_0$; the gray-coding circuitry includes an exclusive-or (XOR) gate for outputting each of $g_{N-2}, g_{N-3} \ldots g_1$, and $g_0$, where an XOR gate for outputting a given $g_i$ takes as input $b_{i+1}$ and $b_i$; and the gray-coding circuitry is configured to output $g_{N-1}=b_{N-1}$. In some embodiments, the gray-decoding circuitry is configured to convert the full gray-coded digital ultrasound signals to the standard binary-coded digital ultrasound signals. In some embodiments, the gray-decoding circuitry is configured to convert a gray coded value $g_{N-1}g_{N-2} \ldots g_1g_0$ to a standard binary coded value $b_{N-1}b_{N-2} \ldots b_1b_0$; the gray-decoding circuitry includes an exclusive-or (XOR) gate for outputting each of $b_{N-2}, b_{N-3} \ldots b_1$, and $b_0$, where an XOR gate for outputting a given $b_i$ takes as input $g_i$ and $b_{i+1}$; and the gray-decoding circuitry is configured to output $b_{N-1}=g_{N-1}$.

In some embodiments, the gray-coding circuitry is configured to convert the standard binary-coded digital ultrasound signals to hybrid gray-coded digital ultrasound signals. In some embodiments, the gray-coding circuitry is configured to convert the standard binary-coded digital ultrasound signals to the hybrid gray-coded digital ultrasound signals such that a transition from mid-code to an adjacent binary code uses a gray code system in that this transition differs by only a single bit, and other transitions use a standard binary code system. In some embodiments, the gray-coding circuitry is configured to convert a standard binary coded value $b_{N-1}b_{N-2} \ldots b_1b_0$ to a gray coded value $g_{N-1}g_{N-2} \ldots g_1g_0$; the gray-coding circuitry includes an exclusive-or (XOR) gate for outputting each of $g_{N-2}$, $g_{N-3} \ldots g_1$, and $g_0$, where an XOR gate for outputting a given $g_i$ takes as input $b_{N-1}$ and $b_1$; and the gray-coding circuitry is configured to output $g_{N-1}=b_{N-1}$. In some embodiments, the gray-decoding circuitry is configured to convert the hybrid gray-coded digital ultrasound signals to the standard binary-coded digital ultrasound signals. In some embodiments, the gray-decoding circuitry is configured to convert a gray coded value $g_{N-1}g_{N-2} \ldots g_1g_0$ to a standard binary coded value $b_{N-1}b_{N-2} \ldots b_1b_0$; the gray-decoding circuitry includes an exclusive-or (XOR) gate for outputting each of $b_{N-2}$, $b_{N-3} \ldots b_1$, and $b_0$, where an XOR gate for outputting a given $b_i$ takes as input $g_i$ and $g_{N-1}$; and the gray-decoding circuitry outputs $b_{N-1}=g_{N-1}$.

Some aspects include a method to perform the actions that the UPU is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 2A illustrates an example physical layout of an ultrasound processing unit (UPU) in the ultrasound-on-chip of FIG. 1, in accordance with certain embodiments described herein;

FIG. 2B illustrates another example physical layout of an ultrasound processing unit (UPU) in the ultrasound-on-chip of FIG. 1, in accordance with certain embodiments described herein;

FIG. 17 illustrates a process for processing ultrasound signals, in accordance with certain embodiments described herein;

DETAILED DESCRIPTION

Figure 1:
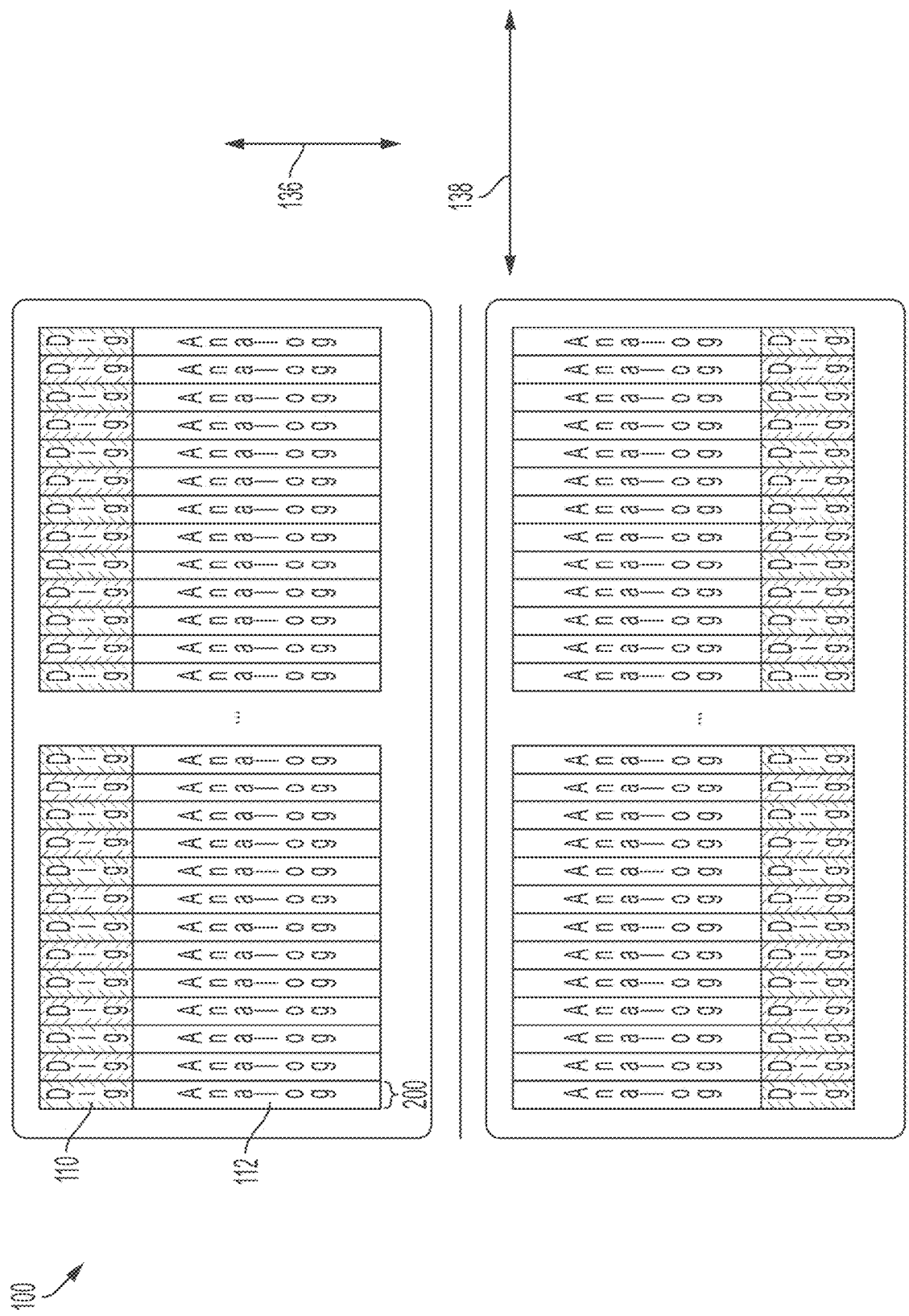
FIG. 1 illustrates an example physical layout of a portion of an ultrasound-on-chip, in accordance with certain embodiments described herein.

When an analog-to-digital converter (ADC) outputs a new binary value that changes digital values on certain bits of its output data bus, this may cause a draw in current from the power supply, power supply noise, and/or transfer of this digital switching activity through capacitive coupling to nearby low bandwidth and/or low amplitude analog signals, which can in turn cause noise in measurements based on the analog signals. As an example, consider that 0 V is inputted to an ADC, and 0 V corresponds to the binary number b'00_0000_0000. A slight amount of noise at the input of the ADC may cause a slightly negative voltage to be inputted to the ADC, and this slightly negative voltage may correspond to the next lowest binary number after b'00 . . . 0 . . . 0000, namely b' 11 . . . 1 . . . 1111 using the two's complement system. Thus, all the digital values on the bits of the data bus may change, and this may exacerbate the problems of power supply current draw, power supply noise, and capacitive coupling of noise to nearby analog circuitry, because this effect may be proportional to the number of bits switching on the data bus. In conventional integrated circuits, analog circuitry may be adjacent to an ADC, and the ADC may be adjacent to digital circuitry. Thus, the data bus from the ADC which is routed to the digital circuitry may not need to be routed over the analog circuitry, and so digital switching on the data bus may be protected from generating noise in analog signals in the analog circuitry.

However, the inventors have developed an ultrasound-on-chip incorporating a large number of ultrasonic transducers along both the elevational and azimuthal dimensions to be incorporated onto an integrated circuit. Such an ultrasound-on-chip can form the core of a handheld ultrasound probe. The large ultrasound transducer array may allow such handheld ultrasound probes to have advanced functionality in terms of imaging techniques and clinical uses. For further description of an ultrasound-on-chip, see U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety. Such ultrasound-on-chips may include multiple analog front-ends (AFEs) for processing signal from ultrasonic transducers. Some embodiments may include multiple AFEs, each including an analog-to-digital converter, tiled along the elevational dimension of the ultrasound-on-chip. Each AFE may be configured to process signals from ultrasonic transducers at different locations along the elevational dimension of the ultrasound-on-chip. The AFEs may share digital circuitry, and this may require data buses from ADCs in certain AFEs to be routed over analog circuits in nearby AFEs in order to reach the shared digital circuitry. This may increase the possibility of digital switching on the data bus generating noise in analog signals in the nearby AFEs' analog circuitry.

Gray coding is a system for ordering binary numbers such that successive binary numbers differ by only bit. In other words, using gray coding, the number of bits that change is proportional to the magnitude of the change in analog value, and not dependent on the actual analog values that are changing. Conventionally, gray coding is used to reduce glitching which may occur due to multiple bits changing when transitioning from one binary number to a successive binary number in standard binary ordering. The inventors have recognized that gray coding the output of an ADC may be helpful for addressing a different problem, namely for minimizing the effect that digital switching on a data bus from an ADC in an AFE may have when the data bus is routed over analog circuitry in nearby AFEs. In general, gray coding the output of an ADC may ensure that the number of bits changing on a data bus due to changes in voltage at the input of the ADC is proportional to the magnitude of the voltage change at the input of the ADC. Thus, in the common case where the voltage at the input of the ADC changes slightly due to noise, fewer bits may change on the data bus with gray coding than with standard binary coding. Because the problems of power supply current draw, power supply noise, and capacitive coupling of noise to nearby analog circuitry may be proportional to the number of bits switching on a data bus, reducing the number of bits changing may reduce these problems. Using the previous example (where 0 V is inputted to an ADC and then a slight amount of noise at the input of the ADC causes a slightly negative voltage to be inputted to the ADC), with a gray coding system that changes only one bit with every successive binary number, the next lowest binary number after b'00 . . . 0 . . . 0000 may be b'10 . . . 0 . . . 0000. Thus, only one bit may change, rather than all the bits changing as with a standard binary system. In this example, compared with standard binary coding, gray coding may reduce the problems of power supply current draw, power supply noise, and capacitive coupling of noise to nearby analog circuitry by approximately a factor of n in an n-bit system due to the factor of n reducing in the number of bits changing on the data bus. Thus, the inventors have implemented an ultrasound-on-chip that includes gray coding of standard binary-coded digital signals from an AFE's ADC, routing of the gray-coded digital signals to shared digital circuitry (which may include routing over other AFEs' analog circuitry), and gray decoding of the gray-coded digital signals to standard binary-coded digital signals prior to processing by the shared digital circuitry.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example physical layout of a portion of an ultrasound-on-chip 100, in accordance with certain embodiments described herein. The ultrasound-on-chip 100 is illustrated in FIG. 1 from a bird's-eye-view. FIG. 1 also illustrates multiple ultrasound processing units (UPUs) 200 in the ultrasound-on-chip 100, an elevational dimension 138 of the ultrasound-on-chip 100, and an azimuthal dimension 136 of the ultrasound-on-chip 100. Each UPU 200 is a self-contained ultrasound processing unit that forms a sub-array of a complete ultrasound imaging array in a scalable fashion. Each UPU 200 includes an analog portion 112 and a digital portion 110, and may include, for example, any or all of high-voltage pulsers to drive ultrasonic transducers to emit ultrasound; analog and mixed-signal receiver channels to receive and digitize ultrasound echoes; digital processing circuitry to filter, compress, and/or beamform the digital data from each channel; and digital sequencing circuit to control and coordinate different parts of the circuitry to work in sync. The analog portion 112 is physically separated from the digital portion 110. FIG. 1 illustrates how multiple UPUs 200 are tiled along an azimuthal dimension 138 of the ultrasound-on-chip 100, and how two rows of the tiled UPUs 200 are arranged along the elevational dimension 136 of the ultrasound-on-chip 100. Ultrasonic transducers (not shown in FIG. 1) may be physically located on top of (i.e., with respect to the depth dimension of the ultrasound-on-chip 100, out of the plane of FIG. 100) the analog portion 112 of each UPU 200, along the elevational dimension 136 of the ultrasound-on-chip 100. Due to the arrangement of the ultrasonic transducers on top of the analog portion 112 of each UPU 200, along the elevational dimension 136 of the ultrasound-on-chip 100, and due to the tiling of the UPUs 200 along the azimuthal dimension 138 of the ultrasound-on-chip 100, ultrasonic transducers may be arranged in an array along the azimuthal dimension 138 and elevational dimensions 136 of the ultrasound-on-chip 100. This allows for azimuthal and elevational beamforming of ultrasound signals received by the ultrasound-on-chip 100.

The physical layout of the ultrasound-on-chip 100 as illustrated in FIG. 1 is non-limiting. For example, in some embodiments, the ultrasound-on-chip 100 may have fewer UPUAs 200 than shown, more or fewer UPUs 200 in each row than shown, and/or more or fewer rows of UPUs 200 than shown. Additionally, while in FIG. 1, the digital portion 110 of each UPU 200 is at the edge of the ultrasound-on-chip 100 and the analog portion 112 of each UPU 200 is at the center of the ultrasound-on-chip 100, in some embodiments the digital portion 110 of each or some of the UPUs 200 may be at the center of the ultrasound-on-chip 100 and the analog portion 112 of each or some UPUs 200 may be at the edge of the ultrasound-on-chip 100.

FIG. 2A illustrates an example physical layout of the ultrasound processing unit (UPU) 200 in the ultrasound-on-chip 100, in accordance with certain embodiments described herein. The UPU 200 is illustrated in FIG. 2A from a bird's-eye-view of the ultrasound-on-chip 100. The UPU includes eight analog front-ends (AFE) 201-208, a block of digital circuitry 210, and eight data buses 244A-251A. The AFEs 201-208 are part of the analog portion 112 of each UPU 200 and the digital circuitry 210 is part of the digital portion 110 of each UPU 200. The AFEs 201-208 are physically arranged in two columns, each of the columns including four AFEs arranged along the elevational dimension 136 of the ultrasound-on-chip 100. The digital circuitry 210 is physically located at one end of the columns along the elevational dimension 138 of the ultrasound-on-chip 100. Each of the AFEs 201-208 may include a pulser, a switch, analog processing circuitry, an ADC, and gray-coding circuitry. Further description of this circuitry may be found with reference to FIG. 3. As described above, ultrasonic transducers (not shown in FIG. 2A) may be physically located on top of (i.e., with respect to the depth dimension of the ultrasound-on-chip 100, out of the plane of FIG. 2) each of the AFEs 201-208. For example, multiple ultrasonic transducers (e.g., eight) may be located each of the AFEs 201-208, and each of the transducers may be coupled to the circuitry of the respective AFE in a multiplexed fashion. Thus, ultrasonic transducers may be arranged on top of each UPU 200, along the elevational dimension 136 of the ultrasound-on-chip 100.

The digital circuitry 210 may include a waveform generator, gray-decoding circuitry, digital processing circuitry, multiplexing circuitry, and multiplexed digital processing circuitry. Further description of this circuitry may be found with reference to FIG. 3. The digital circuitry 210 may be configured to process signals from the AFEs 201-208. Thus, output signals from each of the AFEs 201-208 (e.g., output signals from ADCs) may be routed to the digital circuitry 210, which may process the signals from each of the AFEs 201-208 in a multiplexed fashion. Each of the data buses 244A-251A may be configured to route the digital output of an ADC from each of the AFEs 201-208 to the digital circuitry 210. As can be seen in FIG. 2A, due to the physical layout of the UPU 200, and specifically the arrangement of AFEs 201-208 along the elevational dimension 136 of the ultrasound-on-chip 100, certain of the data buses 244A-251A route digital signals from certain of the AFEs over other AFEs in order to reach the digital circuitry 210. For example, the data bus 251A routing output signals from the AFE 208 passes over the AFEs 205-207 to reach the digital circuitry 210. As described above, digital switching on a data bus passing over analog circuitry in an AFE may introduce noise into analog signals in the AFE. As will be described below, the inventors have recognized that gray coding digital signals outputted from the ADC prior to transmitting the digital signals on the data buses 244A-251A to the digital circuitry 110 may mitigate this effect.

FIG. 2B illustrates another example physical layout of the ultrasound processing unit (UPU) 200 in the ultrasound-on-chip 100, in accordance with certain embodiments described herein. The UPU 200 is illustrated in FIG. 2B from a bird's-eye-view of the ultrasound-on-chip 100. The UPU 200 illustrated in FIG. 2B differs from the UPU 200 illustrated in FIG. 2A in that instead of data buses from each of the AFEs 201-208 extending directly to the digital circuitry 210 as in FIG. 2A, pipelining is used to transmit output data from each of the AFEs 201-208 to the digital circuitry 210. In particular, one of the AFEs may pass its output data to an adjacent AFE, and that AFE may pass the output data from the previous AFE to an adjacent AFE, and so on, until an AFE passes the output data to the digital circuitry 210. Thus, as FIG. 2B illustrates, the data bus 244B passes from the AFE 201 to the digital circuitry 210, the data bus 245B passes from the AFE 202 to the AFE 201, the data bus 246B passes from the AFE 203 to the AFE 202, the data bus 247B passes from the AFE 204 to the AFE 203, the data bus 248B passes from the AFE 205 to the digital circuitry 210, the data bus 249B passes from the AFE 206 to the AFE 205, the data bus 250B passes from the AFE 207 to the AFE 206, and the data bus 251B passes from the AFE 208 to the AFE 207.

As an example of operation of the pipeline, on one clock cycle, the AFE 208 may pass its output data to the AFE 207 over the data bus 251B, the AFE 207 may pass its output data to the AFE 206 over the data bus 250B, the AFE 206 may pass its output data to the AFE 205 over the data bus 249B, and the AFE 205 may pass its output data to the digital circuitry 210 over the data bus 248B. On the next clock cycle, the AFE 207 may pass the AFE 208's output data to the AFE 206 over the data bus 250B, the AFE 206 may pass the AFE 207's output data to the AFE 205 over the data bus 249B, and the AFE 205 may pass the AFE 206's output data to the digital circuitry 210 over the data bus 248B. On the next clock cycle, the AFE 206 may pass the AFE 208's output data to the AFE 205 over the data bus 249B, and the AFE 205 may pass the AFE 207's output data to the digital circuitry 210 over the data bus 248B. On the next clock cycle, the AFE 205 may pass the AFE 208's output data to the digital circuitry 210 over the data bus 248B. When each of the AFEs 205-208 has generated new output data, the process may repeat.

As can be seen in FIG. 2B, due to the physical layout of the UPU 200, and specifically the arrangement of AFEs 201-208 along the elevational dimension 136 of the ultrasound-on-chip 100, certain of the data buses 244B-251B route digital signals from certain of the AFEs over other AFEs in order to reach the digital circuitry 210. For example, the data bus 251B routing output signals from the AFE 208 passes over the AFEs 207-208 to reach the digital circuitry 210. As described above, digital switching on a data bus passing over analog circuitry in an AFE may introduce noise into analog signals in the AFE. As will be described below, the inventors have recognized that gray coding digital signals outputted from the ADC prior to transmitting the digital signals on the data buses 244B-251B to the digital circuitry 110 may mitigate this effect.

The physical layout of the UPU 200 as illustrated in FIGS. 2A-2B is non-limiting. For example, in some embodiments, there may be more or fewer AFEs than shown, more or fewer AFEs per column than shown, and/or more or fewer columns than shown. Additionally, in some embodiments, the data buses may take different paths from the AFEs to the digital circuitry 110 than shown.

Figure 3:
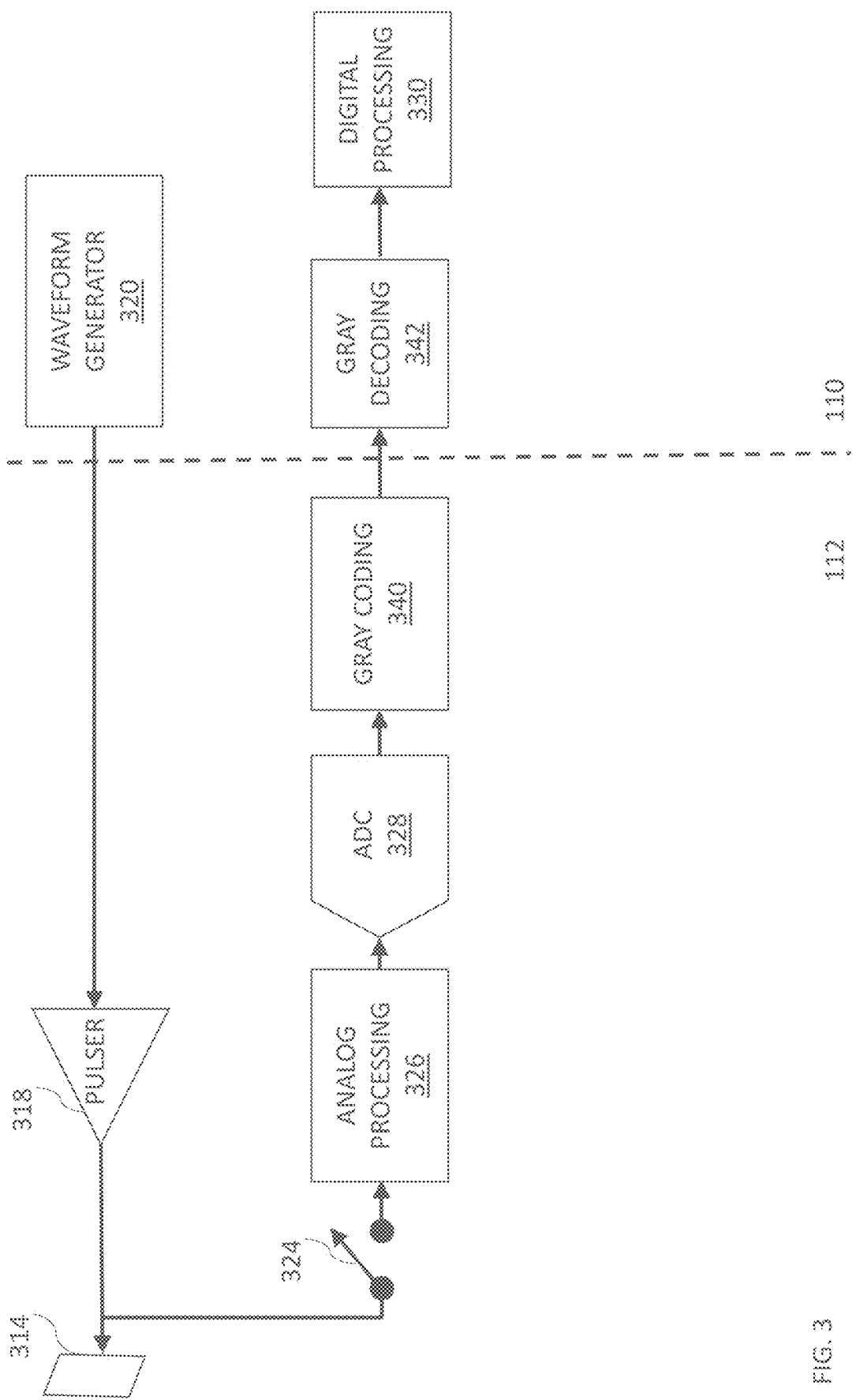
FIG. 3 illustrates an example block diagram of circuitry in the ultrasound-on-chip of FIG. 1, in accordance with certain embodiments described herein.

FIG. 3 illustrates an example block diagram of circuitry in the ultrasound-on-chip 100, in accordance with certain embodiments described herein. The circuitry includes an ultrasonic transducer 314, a pulser 318, a waveform generator 320, a switch 324, analog processing circuitry 326, an analog-to-digital converter (ADC) 328, gray-coding circuitry 340, gray-decoding circuitry 342, and digital processing circuitry 330. There may be at least one ultrasonic transducer 314, pulser 318, switch 324, block of analog processing circuitry 326, ADC 328, block of gray-coding circuitry 340, block of gray decoding circuitry 342, and block of digital processing circuitry 330 for each of the AFEs 201-208 in a UPU 200. As illustrated in FIG. 3, the pulser 318, the switch 324, the analog processing circuitry 326, the ADC 328, and the gray-coding circuitry 340 may be physically located in the analog portion of each UPU 200. The waveform generator 320, the gray-decoding circuitry 342, and the digital processing circuitry 330 may be physically located in the digital portion 110 of a UPU 200.

The waveform generator 320 may be configured to provide a waveform to the pulser 318. The pulser 318 may be configured to output a driving signal corresponding to the received waveform to the ultrasonic transducer 314. When the pulser 318 is driving the ultrasonic transducer 314 (the "transmit phase"), the switch 324 may be open such that the driving signal is not applied to the analog processing circuitry 326.

The ultrasonic transducer 314 may be configured to emit pulsed ultrasonic signals into a subject, such as a patient, in response to the driving signal received from the pulser 318. The pulsed ultrasonic signals may be back-scattered from structures in the body, such as blood cells or muscular tissue, to produce echoes that return to the ultrasonic transducer 314. The ultrasonic transducer 314 may be configured to convert these echoes into electrical signals (i.e., analog ultrasound signals). When the ultrasonic transducer 314 is receiving the echoes (the "receive phase"), the switch 324 may be closed such that the ultrasonic transducer 314 may transmit the analog ultrasound signals representing the received echoes through the switch 324 to the analog processing circuitry 326.

The analog processing circuitry 326 may include, for example, one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, and/or analog averaging circuitry. The analog ultrasound signal output of the analog processing circuitry 326 is outputted to the ADC 328 for conversion to a standard binary-coded digital signals. The ADC 328 may be, for example, a flash ADC, a successive approximation ADC, or a sigma-delta ADC configured to convert analog signals to standard binary-coded digital signals. The standard binary-coded digital ultrasound signal output of the ADC 328 is outputted to the gray-coding circuitry 340 for conversion from standard binary coding to gray coding. The gray-coded digital ultrasound signal output of the gray-coding circuitry 340 is outputted to the gray-decoding circuitry 342 for conversion from gray coding to standard binary coding. The standard binary-coded digital ultrasound signal output of the gray-decoding circuitry 342 is outputted to the digital processing circuitry 330.

The digital processing circuitry 330 may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, and backend processing circuitry. The image formation circuitry may be configured to perform apodization, back projection and/or fast hierarchy back projection, interpolation range migration (e.g., Stolt interpolation) or other Fourier resampling techniques, dynamic focusing techniques, and/or delay and sum techniques, tomographic reconstruction techniques, etc.

As described above, when a data bus routes digital signals from an AFE 201-208 in the analog portion 112 of a UPU 200, over another AFE 201-208 in the analog portion 112 of the UPU 200, and to the digital circuitry 210 in the digital portion 110 of the UPU 200, digital switching on the data bus may introduce noise into analog signals in the AFE the data bus passes over. As illustrated in FIG. 3, the gray-coding circuitry 340 converts the digital output of the ADC 328 from standard binary coding to gray coding prior to the digital output passing from the analog portion 112 of the UPU 200 to the digital portion 110 of the UPU 20. In general, gray coding may ensure that the number of bits changing on a data bus at the output of the ADC 328 due to changes in voltage at the input of the ADC 328 is proportional to the magnitude of the voltage change at the input of the ADC 328. Thus, in the common case where the voltage at the input of the ADC 328 changes slightly due to noise, because fewer bits may change on the data bus with gray coding than with standard binary coding, the problems of power supply current draw, power supply noise, and capacitive coupling of noise to nearby AFEs may be reduced.

Figure 4:
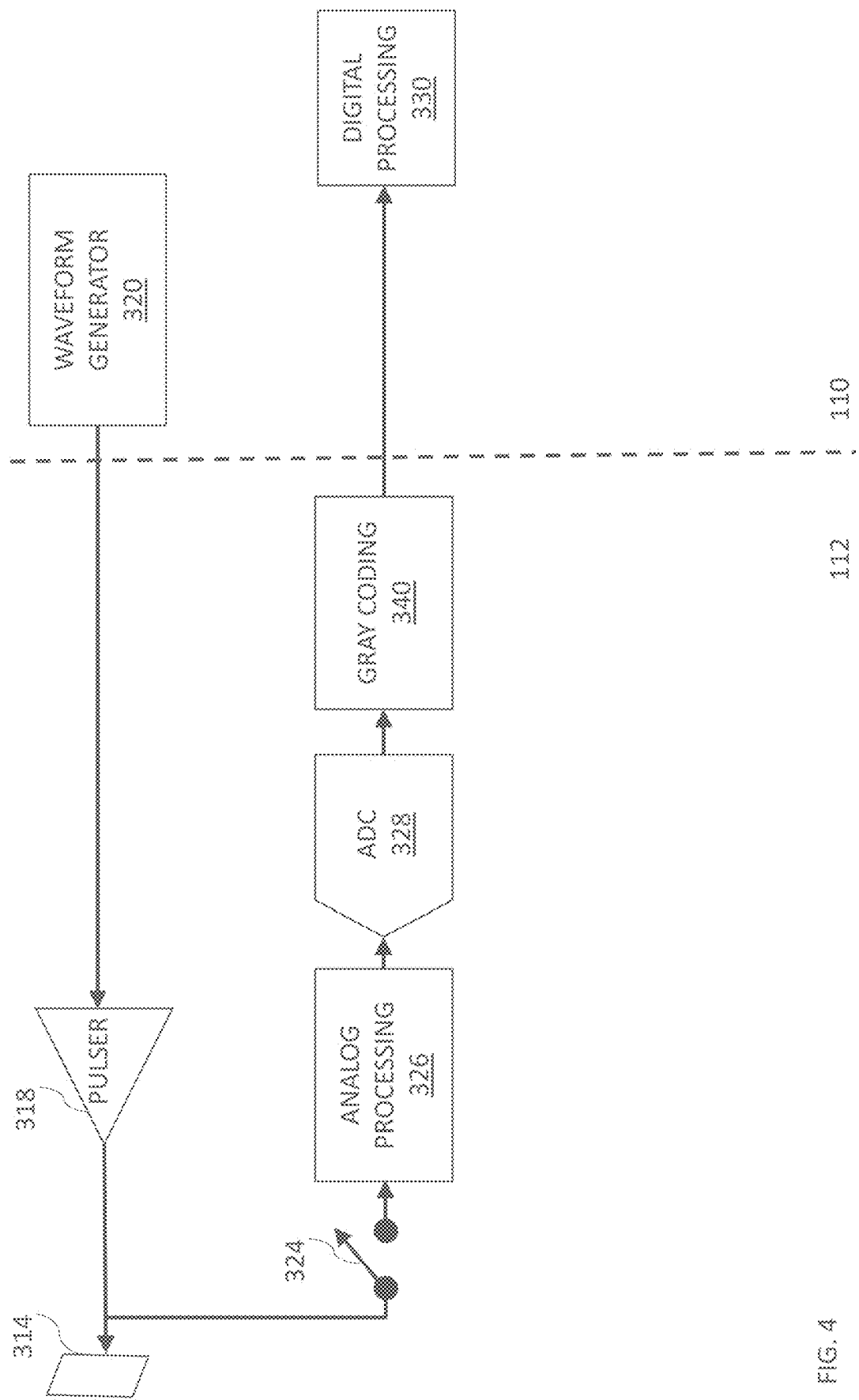
FIG. 4 illustrates another example block diagram of circuitry in the ultrasound-on-chip of FIG. 1, in accordance with certain embodiments described herein.

FIG. 4 illustrates another example block diagram of circuitry in the ultrasound-on-chip 100, in accordance with certain embodiments described herein. FIG. 4 differs from FIG. 3 in that the embodiment of FIG. 4 lacks the gray decoding circuitry 342. In this embodiment, the digital processing circuitry 330 may be configured to process gray-coded digital signals.

Figure 5:
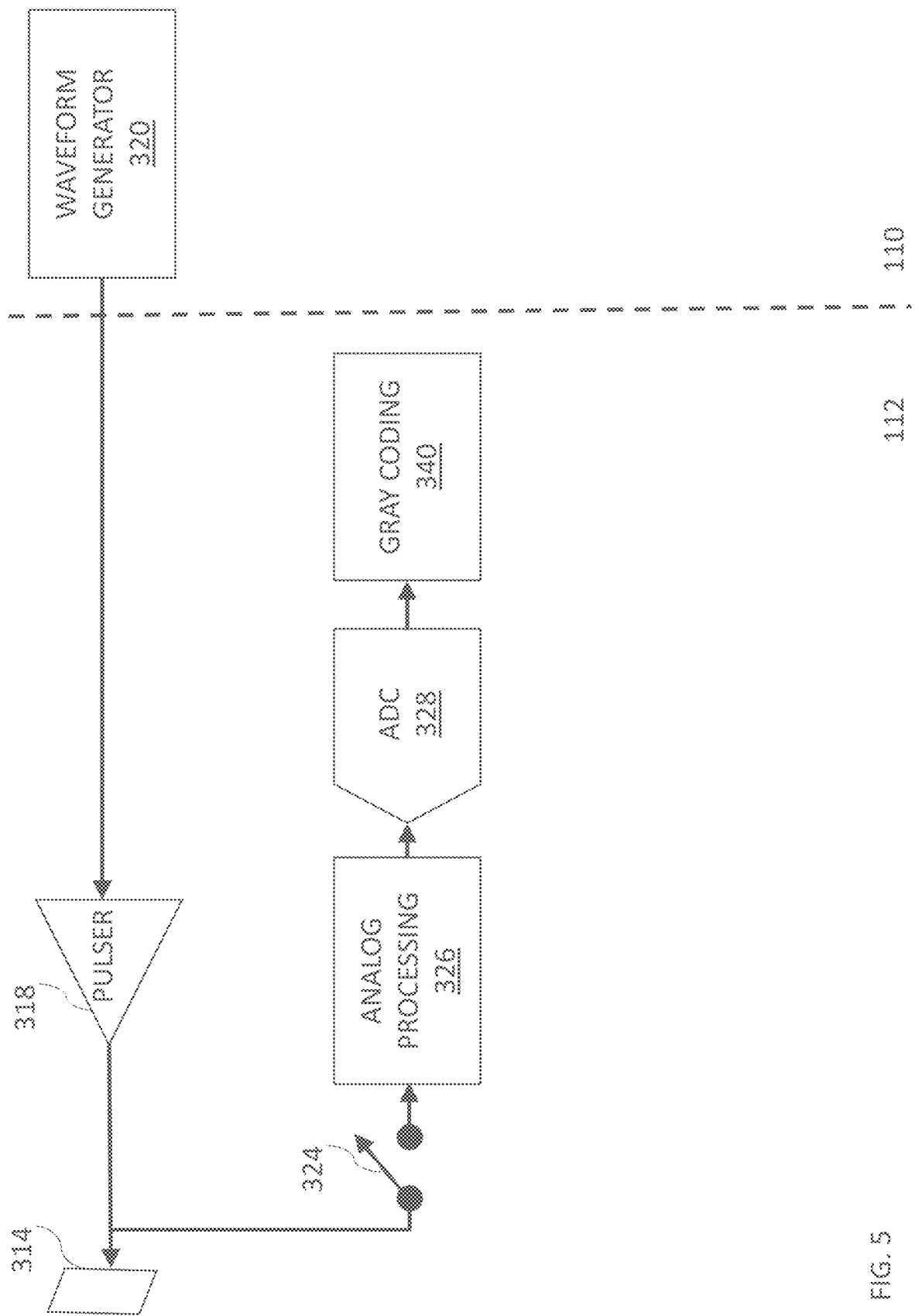
FIG. 5 illustrates another example block diagram of circuitry in the ultrasound-on-chip of FIG. 1, in accordance with certain embodiments described herein.

FIG. 5 illustrates another example block diagram of circuitry in the ultrasound-on-chip 100, in accordance with certain embodiments described herein. FIG. 5 differs from FIG. 3 in that the embodiment of FIG. 5 lacks the gray decoding circuitry 342 and the digital processing circuitry 330. In this embodiment, the output of an AFE (and in particular, the output of the AFE's gray-coding circuitry 340) may not be routed to the digital portion 110 of the UPU 200, but rather may be transmitted off the ultrasound-on-chip 100 to be digitally processed by an off-chip device (e.g., by a field-programmable gate array (FPGA)). The off-chip processing may include gray decoding.

Figure 6:
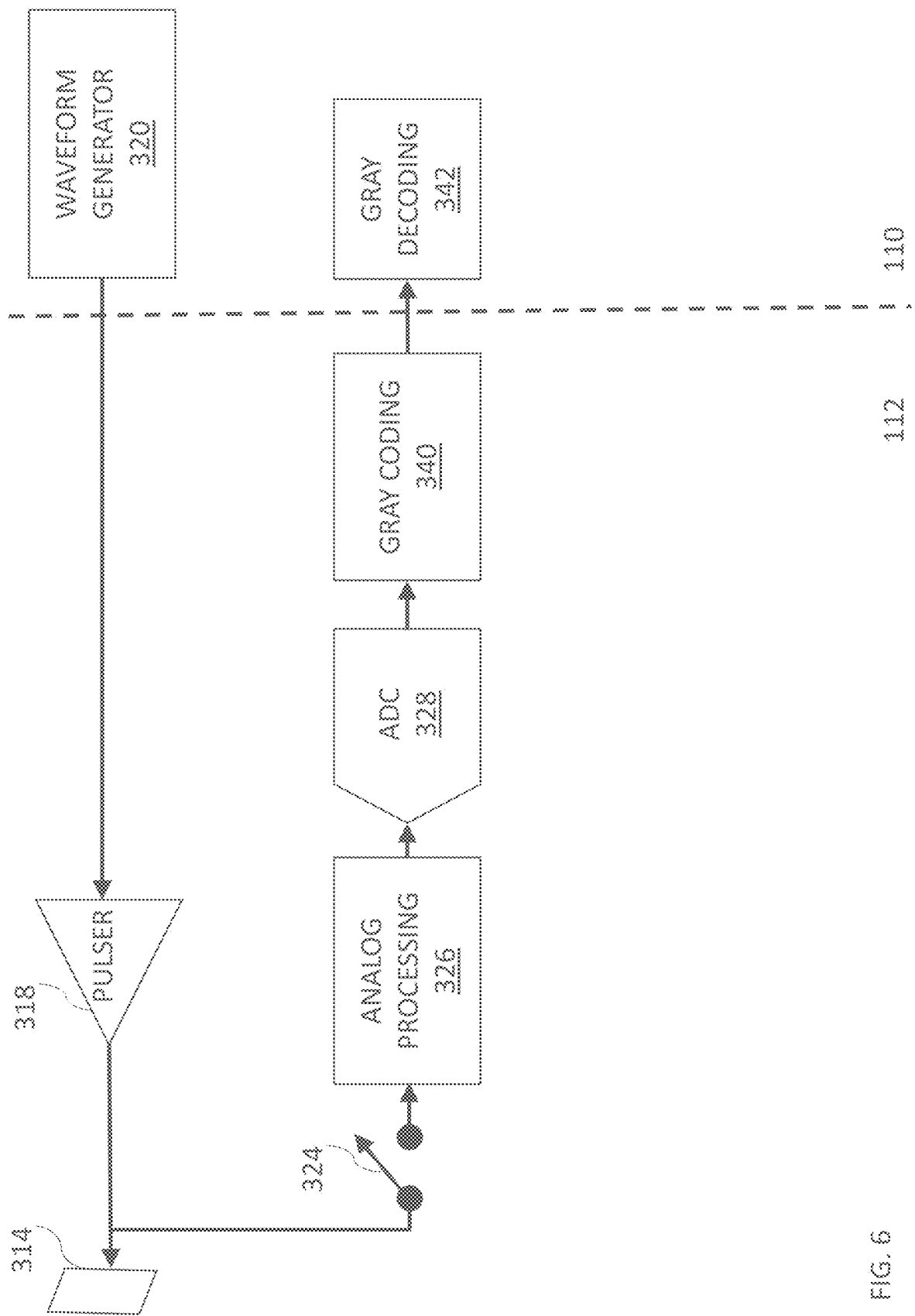
FIG. 6 illustrates another example block diagram of circuitry in the ultrasound-on-chip of FIG. 1, in accordance with certain embodiments described herein.

FIG. 6 illustrates another example block diagram of circuitry in the ultrasound-on-chip 100, in accordance with certain embodiments described herein. FIG. 6 differs from FIG. 3 in that the embodiment of FIG. 6 lacks the digital processing circuitry 330. In this embodiment, the output of the AFE's gray-decoding circuitry 342 may be transmitted off the ultrasound-on-chip 100 to be digitally processed by an off-chip device (e.g., by a field-programmable gate array (FPGA)). Since the data transmitted off the ultrasound-on-a-chip 100 may already be gray decoded by the gray-decoding 342, the off-chip processing may not include gray decoding.

FIGS. 3-6 are non-limiting, and the ultrasound-on-chip 100 may include fewer or more components than shown. For example, there may be addition components interposed between the circuitry illustrated in FIGS. 3-6. However, even if there is, for example, more circuitry interposed between the ADC 328 and the gray-coding circuitry 340, the ADC 328 may still be considered to "output" signals to the gray-coding circuitry 340. In some embodiments, one waveform generator 320 may output to multiple pulsers 318 (e.g., in a multiplexed fashion). In some embodiments, one waveform generator 320 may output to only one pulser 318. In some embodiments, one pulser 318 may output to multiple ultrasonic transducers 314 (e.g., in a multiplexed fashion). In some embodiments, one pulser 318 may output to only one ultrasonic transducer. In some embodiments, multiple ultrasonic transducers 314 may output to one block of analog processing circuitry 326 (e.g., in a multiplexed fashion). In some embodiments, only one ultrasonic transducer 314 may output to one block of analog processing circuitry 326. In some embodiments, the ultrasonic transducer 314 may be configured to output to the ADC 328, and the analog processing circuitry 326 may be absent. In some embodiments, instead of the ADC 328 and the gray-coding circuitry 340, circuitry may directly convert the analog output of the analog processing circuitry 326 to gray-coded digital output. In some embodiments, there may be multiple blocks of the digital processing circuitry 330, and the standard binary-coded digital ultrasound signals from the gray-decoding circuitry 342 may be output to a dedicated block of the digital processing circuitry 330. In some embodiments, there may be multiple blocks of the digital processing circuitry 330, and groups of the standard binary-coded digital ultrasound signals may each be multiplexed to one of the multiple blocks of the digital processing circuitry 330. In some embodiments, all the standard binary-coded digital ultrasound signals may be multiplexed to one block of the digital processing circuitry 330. In some embodiments, there may be multiple blocks of one type of digital processing circuitry (e.g., a dedicated block for each standard binary-coded digital ultrasound signal, or a block to which a group of standard binary-coded digital ultrasound signals is multiplexed) including certain circuitry, and then all the processed signals may be multiplexed to one block of a second type of digital processing circuitry. For example, the first type of digital processing circuitry may include one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, and digital multiplying circuitry, and the second type of digital processing circuitry may include requantization circuitry, waveform removal circuitry, image formation circuitry, and backend processing circuitry.

Figure 7:
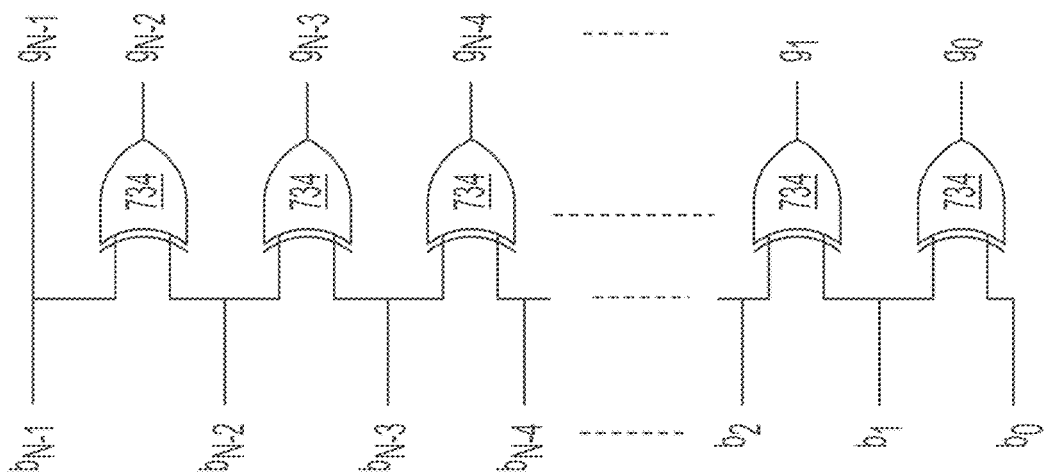
FIG. 7 illustrates example gray-coding circuitry, in accordance with certain embodiments described herein.

FIG. 7 illustrates example gray-coding circuitry 740, in accordance with certain embodiments described herein. The gray-coding circuitry 740 may be used as the gray-coding circuitry 340. In particular, FIG. 7 illustrates gray-coding circuitry 740 for converting a binary coded value $b_{N-1}b_{N-2} \ldots b_1b_0$ to a gray coded value $g_{N-1}g_{N-2} \ldots g_1g_0$. The gray-coding circuitry 740 includes an exclusive-or (XOR) gate 734 for outputting each of $g_{N-2}$, $g_{N-3} \ldots g_1$, and $g_0$, where the XOR gate 734 for outputting a given $g_i$ takes as input $b_{i+1}$ and $b_i$. The gray-coding circuitry 740 outputs $g_{N-1}=b_{N-1}$.

Figure 8:
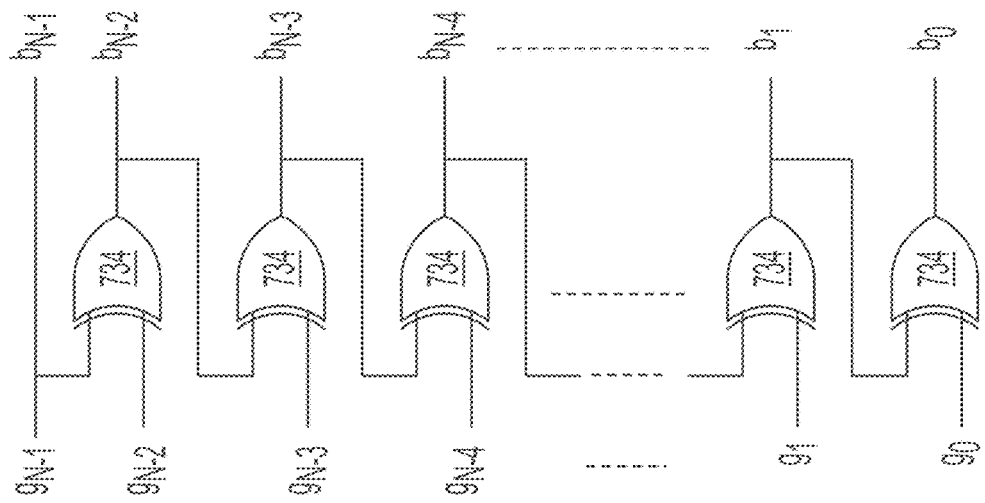
FIG. 8 illustrates example gray-decoding circuitry, in accordance with certain embodiments described herein.

FIG. 8 illustrates example gray-decoding circuitry 842, in accordance with certain embodiments described herein. The gray-decoding circuitry 842 may be used as the gray-decoding circuitry 342. In particular, FIG. 8 illustrates gray-decoding circuitry 842 for converting a gray coded value $g_{N-1}g_{N-2} \ldots g_1g_0$ that was coded with the gray coding system of the gray-coding circuitry 740 to a binary coded value $b_{N-1}b_{N-2} \ldots b_1b_0$. The gray-decoding circuitry 842 includes an exclusive-or (XOR) gate 734 for outputting each of $b_{N-2}$, $b_{N-3} \ldots b_1$, and $b_0$, where the XOR gate 734 for outputting a given $b_i$ takes as input $g_i$ and $b_{i+1}$. The gray-decoding circuitry 842 outputs $b_{N-1}=g_{N-1}$.

Table 1 illustrates example correspondences between decimal values, binary values, and gray coded values using the gray coding system of the gray-coding circuitry 740. In Table 1, n bits are used.

It should be appreciated that under the gray coding system of the gray-coding circuitry 740, every transition from one binary code to an adjacent binary code differs by only a single bit. This may be considered a full gray code system. Thus, regardless of actual analog voltage values being converted by the ADC 328, the number of bits changing on the data bus at the output of the gray-coding circuitry 740 due to changes in the analog voltage value at the input of the ADC 328 may be proportional to the change in voltage value. A drawback of the gray coding system of the gray-coding circuitry 740 may be that for decoding a given $g_i$ to $b_i$ for i between 0 and N−3, the gray-decoding circuitry 842 may require the result of the conversion from $g_{i+1}$ to $b_{i+1}$. Thus, the depth of the XOR gates 734 may be N−1, which may constrain the timing requirements for the gray-decoding circuitry 842 as N increases.

Figure 9:
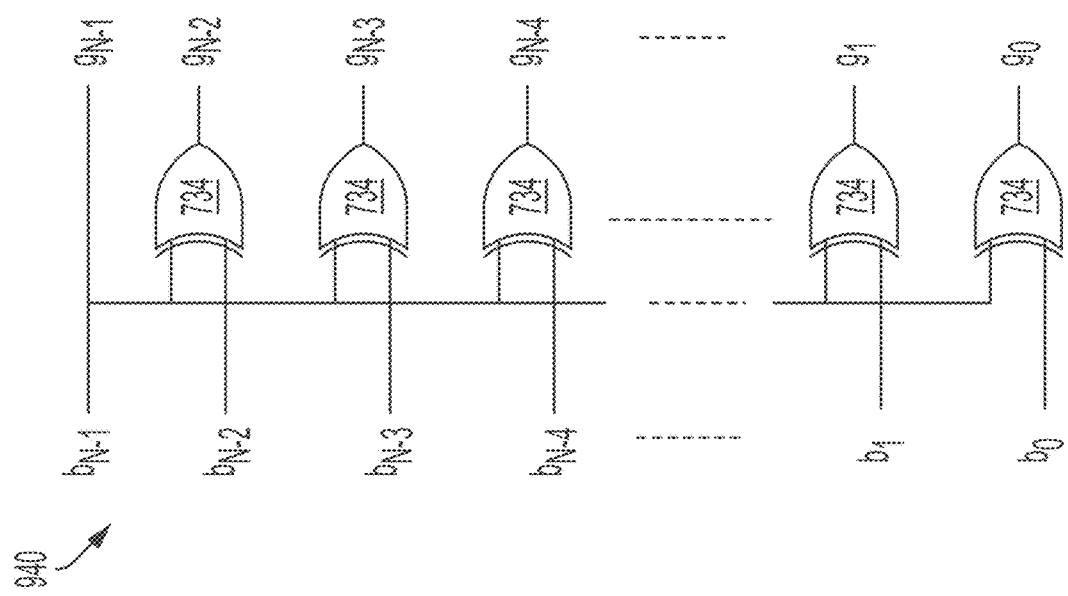
FIG. 9 illustrates another example of gray-coding circuitry, in accordance with certain embodiments described herein.

FIG. 9 illustrates another example of gray-coding circuitry 940, in accordance with certain embodiments described herein. The gray-coding circuitry 940 may be used as the gray-coding circuitry 340. In particular, FIG. 9 illustrates gray-coding circuitry 940 for converting a binary coded value $b_{N-1}b_{N-2} \ldots b_1b_0$ to a gray coded value $g_{N-1}g_{N-2} \ldots g_1g_0$. The gray-coding circuitry 940 includes an exclusive-or (XOR) gate 734 for outputting each of $g_{N-2}$, $g_{N-3} \ldots g_1$, and $g_0$, where the XOR gate 734 for outputting a given $g_i$ takes as input $b_{N-1}$ and $b_i$. The gray-coding circuitry 940 outputs $g_{N-1}=b_{N-1}$.

Figure 10:
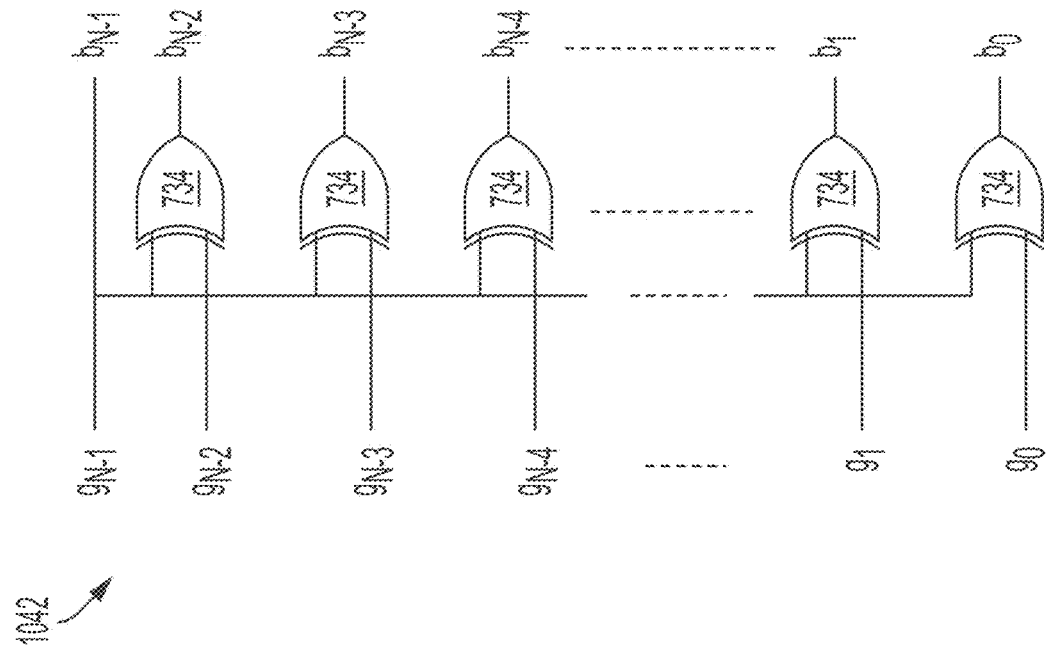
FIG. 10 illustrates another example gray-decoding circuitry, in accordance with certain embodiments described herein.

FIG. 10 illustrates another example of gray-decoding circuitry 1042, in accordance with certain embodiments described herein. The gray-decoding circuitry 1042 may be used as the gray-decoding circuitry 342. In particular, FIG. 10 illustrates gray-decoding circuitry 1042 for converting a gray coded value $g_{N-1}g_{N-2} \ldots g_1g_0$ that was coded with the gray coding system of the gray-coding circuitry 940 to a binary coded value $b_{N-1}b_{N-2} \ldots b_1b_0$. The gray-decoding circuitry 1042 includes an exclusive-or (XOR) gate 734 for outputting each of $b_{N-2}$, $b_{N-3} \ldots b_1$, and $b_0$, where the XOR gate 734 for outputting a given $b_i$ takes as input $g_i$ and $g_{N-1}$. The gray-decoding circuitry 1042 outputs $b_{N-1}=g_{N-1}$.

Table 2 illustrates example correspondences between decimal values, binary values, and gray coded values using the gray coding system of the gray-coding circuitry 940. In Table 2, n bits are used.

TABLE 1

Example correspondences between decimal values, binary values, of gray coded values using the gray coding system of the gray-coding circuitry 740.

| Decimal | Binary | Gray Coded |
| --- | --- | --- |
| $2^{n-1} - 8$ | 01 ... 11 11 ... 1000 | 010 ... 00 00 ... 0100 |
| $2^{n-1} - 7$ | 01 ... 11 11 ... 1001 | 010 ... 00 00 ... 0101 |
| $2^{n-1} - 6$ | 01 ... 11 11 ... 1010 | 010 ... 00 00 ... 0111 |
| $2^{n-1} - 5$ | 01 ... 11 11 ... 1011 | 010 ... 00 00 ... 0110 |
| $2^{n-1} - 4$ | 01 ... 11 11 ... 1100 | 010 ... 00 00 ... 0010 |
| $2^{n-1} - 3$ | 01 ... 11 11 ... 1101 | 010 ... 00 00 ... 0011 |
| $2^{n-1} - 2$ | 01 ... 11 11 ... 1110 | 010 ... 00 00 ... 0001 |
| $2^{n-1} - 1$ | 01 ... 11 11 ... 1111 | 010 ... 00 00 ... 0000 |
| $2^{n-1}$ | 10 ... 00 00 ... 0000 | 110 ... 00 00 ... 0000 |
| $2^{n-1} + 1$ | 10 ... 00 00 ... 0001 | 110 ... 00 00 ... 0001 |
| $2^{n-1} + 2$ | 10 ... 00 00 ... 0010 | 110 ... 00 00 ... 0011 |
| $2^{n-1} + 3$ | 10 ... 00 00 ... 0011 | 110 ... 00 00 ... 0010 |
| $2^{n-1} + 4$ | 10 ... 00 00 ... 0100 | 110 ... 00 00 ... 0110 |
| $2^{n-1} + 5$ | 10 ... 00 00 ... 0101 | 110 ... 00 00 ... 0111 |
| $2^{n-1} + 6$ | 10 ... 00 00 ... 0110 | 110 ... 00 00 ... 0101 |
| $2^{n-1} + 7$ | 10 ... 00 00 ... 0111 | 110 ... 00 00 ... 0100 |

TABLE 2

Example correspondences between decimal values, binary values, of gray coded values using the gray coding system of the gray-coding circuitry 940.

| Decimal | Binary | Gray Coded |
| --- | --- | --- |
| $2^{n-1} - 8$ | 01 ... 11 11 ... 1000 | 01 ... 11 11 ... 1000 |
| $2^{n-1} - 7$ | 01 ... 11 11 ... 1001 | 01 ... 11 11 ... 1001 |
| $2^{n-1} - 6$ | 01 ... 11 11 ... 1010 | 01 ... 11 11 ... 1010 |
| $2^{n-1} - 5$ | 01 ... 11 11 ... 1011 | 01 ... 11 11 ... 1011 |
| $2^{n-1} - 4$ | 01 ... 11 11 ... 1100 | 01 ... 11 11 ... 1100 |
| $2^{n-1} - 3$ | 01 ... 11 11 ... 1101 | 01 ... 11 11 ... 1101 |
| $2^{n-1} - 2$ | 01 ... 11 11 ... 1110 | 01 ... 11 11 ... 1110 |
| $2^{n-1} - 1$ | 01 ... 11 11 ... 1111 | 01 ... 11 11 ... 1111 |
| $2^{n-1}$ | 10 ... 00 00 ... 0000 | 11 ... 11 11 ... 1111 |
| $2^{n-1} + 1$ | 10 ... 00 00 ... 0001 | 11 ... 11 11 ... 1110 |
| $2^{n-1} + 2$ | 10 ... 00 00 ... 0010 | 11 ... 11 11 ... 1101 |
| $2^{n-1} + 3$ | 10 ... 00 00 ... 0011 | 11 ... 11 11 ... 1100 |
| $2^{n-1} + 4$ | 10 ... 00 00 ... 0100 | 11 ... 11 11 ... 1011 |
| $2^{n-1} + 5$ | 10 ... 00 00 ... 0101 | 11 ... 11 11 ... 1010 |
| $2^{n-1} + 6$ | 10 ... 00 00 ... 0110 | 11 ... 11 11 ... 1001 |
| $2^{n-1} + 7$ | 10 ... 00 00 ... 0111 | 11 ... 11 11 ... 1000 |

It should be appreciated that under the gray coding system of the gray-coding circuitry 940, the transition from mid-code to an adjacent binary code uses a gray code system in that this transition differs by only a single bit. Other transitions use a standard binary code system in which a transition from one binary code to an adjacent binary code may differ by multiple bits. This may be considered a hybrid gray code system with only the most significant bit (MSB) using gray coding. Thus, when the analog voltage value at the input of the ADC 328 is at mid-scale and the change in voltage is equivalent to one binary code, only one bit on the data bus at the output of the gray-coding circuitry 940 may change. It should be appreciated that it may be a common transition at the input of the ADC 328 for the voltage value to be at mid-scale and for the change in voltage to be equivalent to one binary code. It should also be appreciated that when using standard binary coding rather than gray coding, a change in voltage corresponding to one binary code from the mid-scale voltage may cause a large number of bits to change compared to the number of bits that may change for other transitions. A drawback of the gray coding system of the gray-coding circuitry 940 compared with the system of the gray-coding circuitry 740 may be that for transitions corresponding to one binary code at other analog voltages, more than one bit may change. A benefit of the gray coding system of the gray-coding circuitry 940 compared with the system of the gray-decoding circuitry 842 may be that for decoding a given $g_i$ to $b_i$, the gray-decoding circuitry 1042 may not require the result of the conversion from $g_{i+1}$ to $b_{i+1}$. Thus, the depth of the XOR gates 734 may be 1, which may relieve the timing requirements for the gray-decoding circuitry 1042 compared with the gray-decoding circuitry 842.

Figure 11:
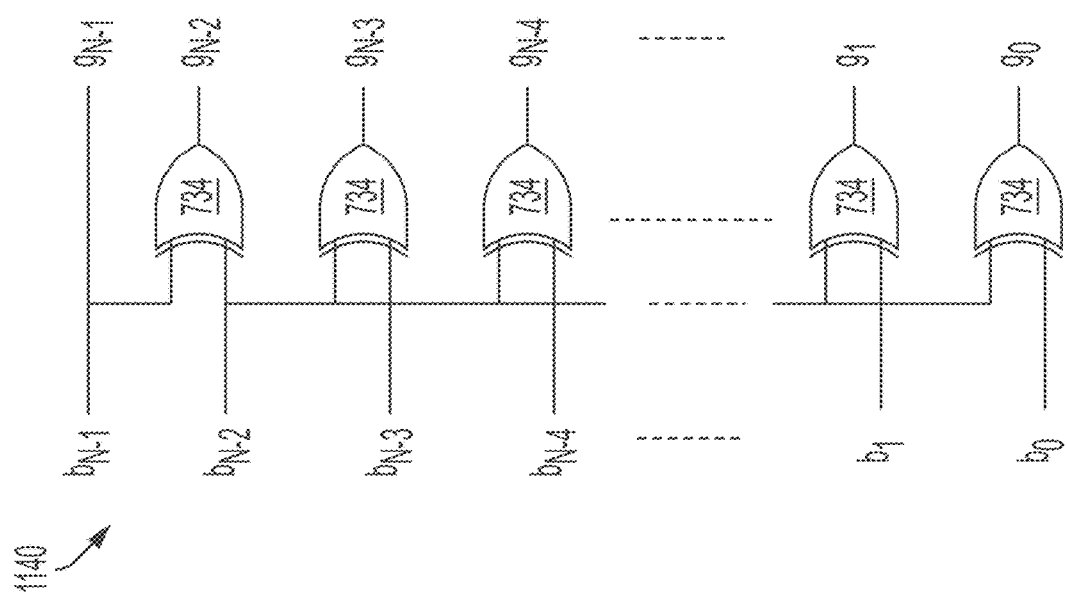
FIG. 11 illustrates another example of gray-coding circuitry, in accordance with certain embodiments described herein.

FIG. 11 illustrates another example of gray-coding circuitry 1140, in accordance with certain embodiments described herein. The gray-coding circuitry 1140 may be used as the gray-coding circuitry 340. In particular, FIG. 11 illustrates gray-coding circuitry 1140 for converting a binary coded value $b_{N-1}b_{N-2} \ldots b_1b_0$ to a gray coded value $g_{N-1}g_{N-2} \ldots g_1g_0$. The gray-coding circuitry 1140 includes an exclusive-or (XOR) gate 734 for outputting each of $g_{N-2}$, $g_{N-3} \ldots g_1$, and $g_0$. The XOR gate 734 for outputting a given $g_i$ from $g_{N-3}$ to $g_0$ takes as input $b_{N-2}$ and $b_1$. The XOR gate 734 for outputting $g_{N-2}$ takes as input $b_{N-1}$ and $b_{N-2}$. The gray-coding circuitry 1140 outputs $g_{N-1}=b_{N-1}$.

Figure 12:
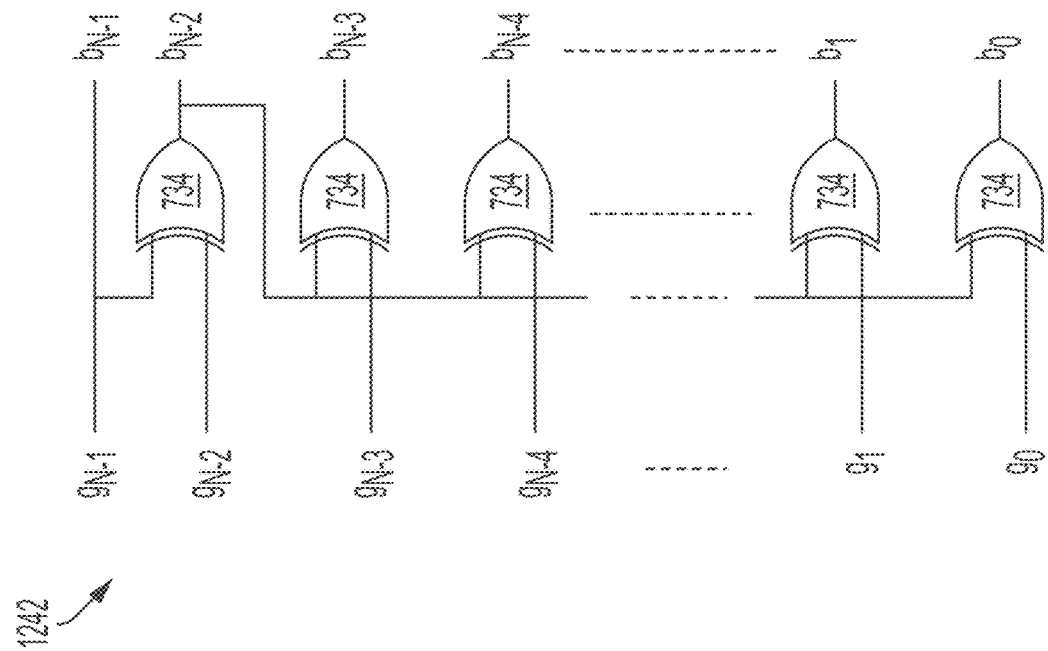
FIG. 12 illustrates another example gray-decoding circuitry, in accordance with certain embodiments described herein.

FIG. 12 illustrates another example of gray-decoding circuitry 1242, in accordance with certain embodiments described herein. The gray-decoding circuitry 1242 may be used as the gray-decoding circuitry 342. In particular, FIG. 12 illustrates gray-decoding circuitry 1242 for converting a gray coded value $g_{N-1}g_{N-2} \ldots g_1g_0$ that was coded with the gray coding system of the gray-coding circuitry 1140 to a binary coded value $b_{N-1}b_{N-2} \ldots b_1b_0$. The gray-decoding circuitry 1242 includes an exclusive-or (XOR) gate 734 for outputting each of $b_{N-2}$, $b_{N-3} \ldots b_1$, and $b_0$. The XOR gate 734 for outputting a given $b_i$ from $b_{N-3}$ to $b_0$ takes as input $b_{N-2}$ and $g_i$. The XOR gate 734 for outputting $b_{N-2}$ takes as input $g_{N-1}$ and $g_{N-2}$. The gray-decoding circuitry 1242 outputs $b_{N-1}=g_{N-1}$.

Table 3 illustrates example correspondences between decimal values, binary values, and gray coded values using the gray coding system of the gray-coding circuitry 1140. In Table 3, n bits are used.

TABLE 3

Example correspondences between decimal values, binary values, of gray coded values using the gray coding system of the gray-coding circuitry 1140.

| Decimal | Binary | Gray Coded |
|---|---|---|
| $2^{n-2} - 3$ | 001 ... 11 11 ... 1101 | 001 ... 11 11 ... 1101 |
| $2^{n-2} - 2$ | 001 ... 11 11 ... 1110 | 001 ... 11 11 ... 1110 |
| $2^{n-2} - 1$ | 001 ... 11 11 ... 1111 | 001 ... 11 11 ... 1111 |
| $2^{n-2}$ | 010 ... 00 00 ... 0000 | 011 ... 11 11 ... 1111 |
| $2^{n-2} + 1$ | 010 ... 00 00 ... 0001 | 011 ... 11 11 ... 1110 |
| $2^{n-2} + 2$ | 010 ... 00 00 ... 0010 | 011 ... 11 11 ... 1101 |
| $2^{n-1} - 3$ | 011 ... 11 11 ... 1101 | 010 ... 00 00 ... 0010 |
| $2^{n-1} - 2$ | 011 ... 11 11 ... 1110 | 010 ... 00 00 ... 0001 |
| $2^{n-1} - 1$ | 011 ... 11 11 ... 1111 | 010 ... 00 00 ... 0000 |
| $2^{n-1}$ | 100 ... 00 00 ... 0000 | 110 ... 00 00 ... 0000 |
| $2^{n-1} + 1$ | 100 ... 00 00 ... 0001 | 110 ... 00 00 ... 0001 |
| $2^{n-1} + 2$ | 100 ... 00 00 ... 0010 | 110 ... 00 00 ... 0010 |
| $3 * 2^{n-2} - 3$ | 101 ... 11 11 ... 1101 | 111 ... 11 11 ... 1101 |
| $3 * 2^{n-2} - 2$ | 101 ... 11 11 ... 1110 | 111 ... 11 11 ... 1110 |
| $3 * 2^{n-2} - 1$ | 101 ... 11 11 ... 1111 | 111 ... 11 11 ... 1111 |
| $3 * 2^{n-2}$ | 110 ... 00 00 ... 0000 | 101 ... 11 11 ... 1111 |
| $3 * 2^{n-2} + 1$ | 110 ... 00 00 ... 0001 | 101 ... 11 11 ... 1110 |
| $3 * 2^{n-2} + 2$ | 110 ... 00 00 ... 0010 | 101 ... 11 11 ... 1101 |
| $2^n - 3$ | 111 ... 11 11 ... 1101 | 100 ... 00 00 ... 0010 |
| $2^n - 2$ | 111 ... 11 11 ... 1110 | 100 ... 00 00 ... 0001 |
| $2^n - 1$ | 111 ... 11 11 ... 1111 | 100 ... 00 00 ... 0000 |

It should be appreciated that under the gray coding system of the gray-coding circuitry 1140, the transitions from quarter code, mid-code, or three-quarters code to an adjacent binary code use a gray code system in that these transitions differ by only a single bit. Other transitions use a standard binary code system in which a transition from one decimal code to an adjacent decimal code may correspond to a transition from one binary code to another binary code that differs by multiple bits. This may be considered a hybrid gray code system with the most significant bit (MSB) and the second most significant bit (MSB−1) using gray coding. Thus, when the analog voltage value at the input of the ADC 328 is at quarter scale, mid-scale, or three-quarters scale, and the change in voltage is equivalent to one binary code, only one bit on the data bus at the output of the gray-coding circuitry 1140 may change. Accordingly, more transitions than the gray coding system of the gray-coding circuitry 940 but fewer transitions than the gray coding system of the gray-coding circuitry 740 may still have the benefits of gray coding in general. It should be appreciated that when using standard binary coding rather than gray coding, a change in voltage corresponding to one binary code from the quarter scale, mid-scale, or three-quarters scale voltage may cause a large number of bits to change compared to the number of bits that may change for other transitions. It should also be appreciated that the gray-decoding circuitry 1042 may only require the result of the conversion from $g_{N-1}$ to $b_{N-1}$ for decoding a given $g_i$ to $b_i$ for i between 0 and N−3. Thus, the depth of the XOR gates 734 may be 2, which may be an incremental constraint on the timing requirements for the gray-decoding circuitry 1242 compared with the gray-decoding circuitry 1042, but less stringent than the timing requirements of the gray-decoding circuitry 842.

Figure 13:
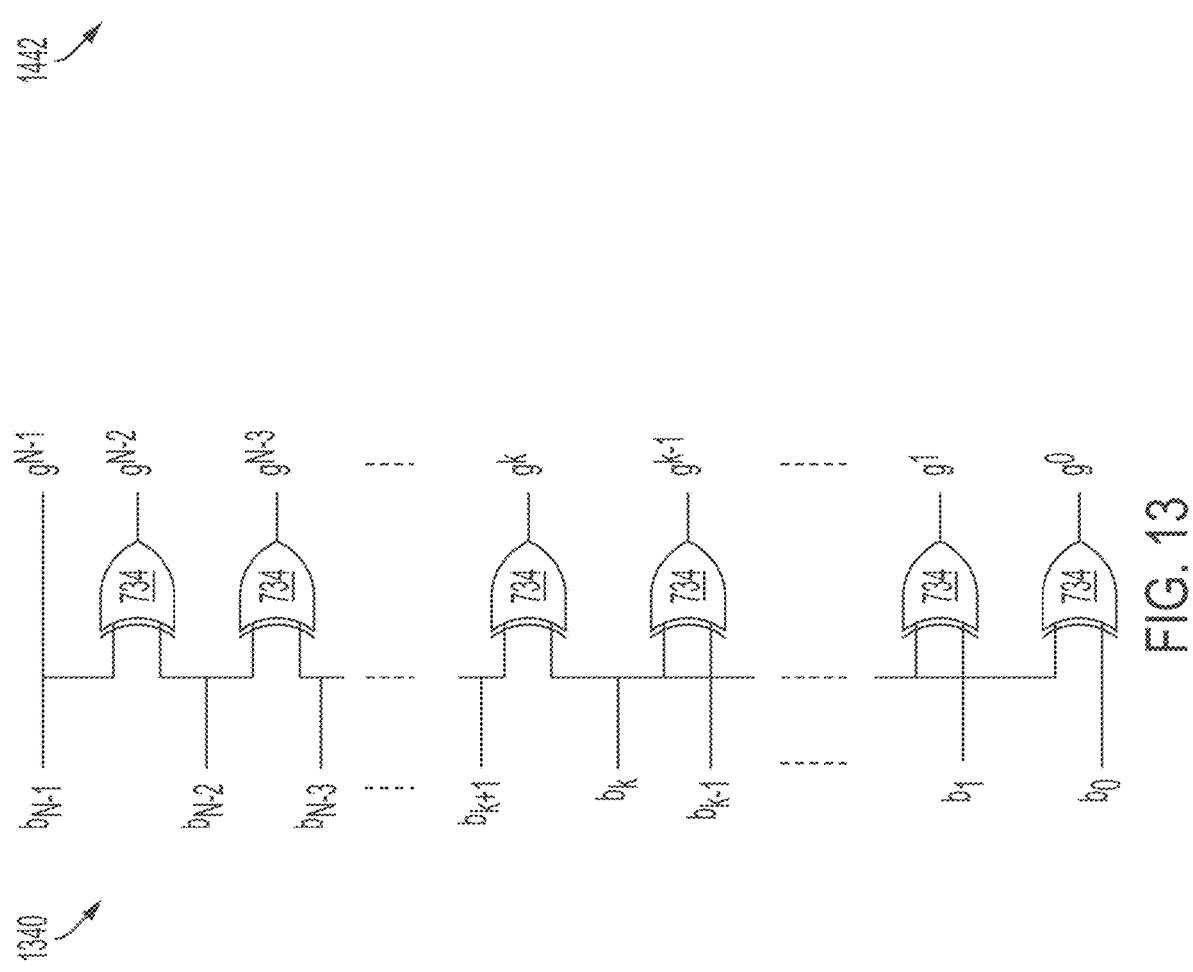
FIG. 13 illustrates another example of gray-coding circuitry, in accordance with certain embodiments described herein.

FIG. 13 illustrates another example of gray-coding circuitry 1340, in accordance with certain embodiments described herein. The gray-coding circuitry 1340 may be used as the gray-coding circuitry 340. In particular, FIG. 13 illustrates gray-coding circuitry 1340 for converting a binary coded value $b_{N-1}b_{N-2} \ldots b_1b_0$ to a gray coded value $g_{N-1}g_{N-2} \ldots g_1g_0$ using hybrid gray coding with the k least significant bits using standard binary coding and the remaining bits using gray coding. Thus, this may be considered a generalization of the gray coding/de-coding of FIGS. 11-12. The gray-coding circuitry 1340 includes an XOR gate 734 for outputting each of $g_{N-2}$, $g_{N-3}$ ... $g_1$, and $g_0$. The XOR gate 734 for outputting a given $g_i$ from $g_{k-1}$ to $g_0$ takes as input $b_k$ and $b_i$. The XOR gate 734 for outputting a given $g_i$ from $g_{N-2}$ through $g_k$ takes as input $b_i$ and $b_{i+1}$. The gray-coding circuitry 1340 outputs $g_{N-1}=b_{N-1}$.

Figure 14:
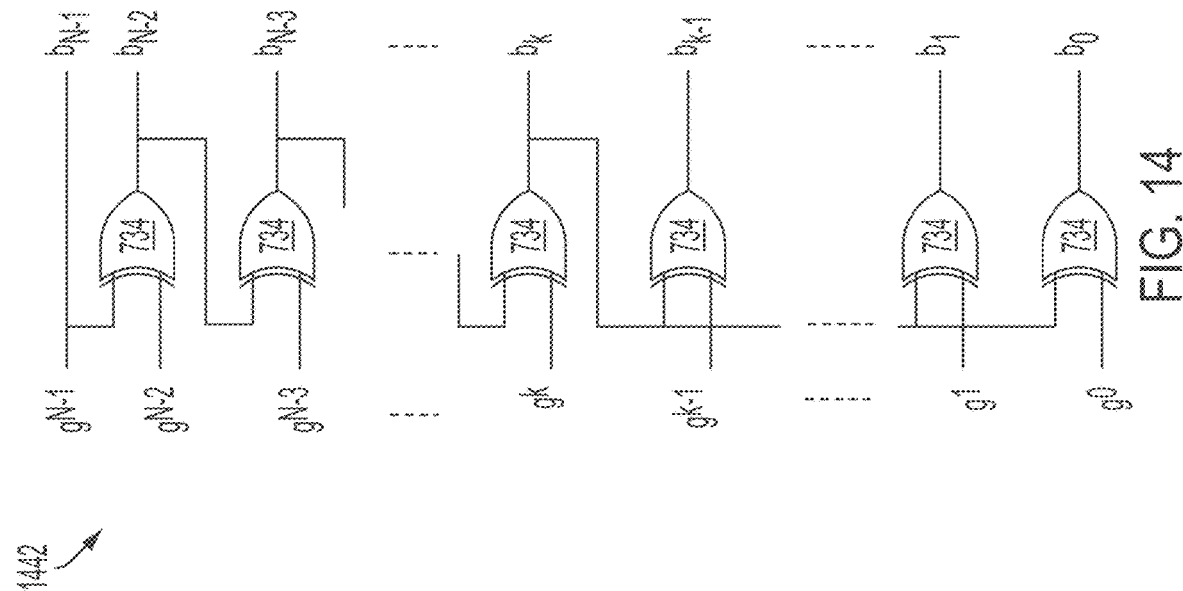
FIG. 14 illustrates another example gray-decoding circuitry, in accordance with certain embodiments described herein.

FIG. 14 illustrates another example of gray-decoding circuitry 1442, in accordance with certain embodiments described herein. The gray-decoding circuitry 1442 may be used as the gray-decoding circuitry 342. In particular, FIG. 14 illustrates gray-decoding circuitry 1442 for converting a gray coded value $g_{N-1}g_{N-2}$ ... $g_1g_0$ that was coded with the gray coding system of the gray-coding circuitry 1340 to a binary coded value $b_{N-1}b_{N-2}$ ... $b_1b_0$. The gray-decoding circuitry for decoding such hybrid gray coding includes an XOR gate 734 for outputting each of $b_{N-2}$, $b_{N-3}$ ... $b_1$, and $b_0$. The XOR gate 734 for outputting a given $b_i$ from $b_{k-1}$ to $b_0$ takes as input $b_k$ and $g_i$. The XOR gate 734 for outputting a given $b_i$ from $b_{N-2}$ to $b_k$ takes as input $g_i$ and $b_{i+1}$. The gray-decoding circuitry 1442 outputs $b_{N-1}=g_{N-1}$.

Table 4 illustrates example correspondences between decimal values, binary values, and gray coded values using the gray coding system of the gray-coding circuitry 1340. In Table 4, n bits are used.

TABLE 4

Example correspondences between decimal values, binary values, of gray coded values using the gray coding system of the gray-coding circuitry 1340.

| | | |
|---|---|---|
| 0 | 00 ... 00 00 ... 00 | 00 ... 00 00 ... 00 |
| 1 | 00 ... 00 00 ... 01 | 00 ... 00 00 ... 01 |
| 2 | 00 ... 00 00 ... 10 | 00 ... 00 00 ... 10 |
| ... | ... | ... |
| $2^k - 1$ | 00 ... 00 11 ... 11 | 00 ... 00 11 ... 11 |
| $2^k$ | 00 ... 01 00 ... 00 | 00 ... 01 11 ... 11 |
| $2^k + 1$ | 00 ... 01 00 ... 01 | 00 ... 01 11 ... 10 |
| ... | ... | ... |
| $2^{k+1}$ | 0 ... 010 00 ... 00 | 0 ... 011 00 ... 00 |
| ... | ... | ... |
| $\Sigma_{i=0}^{n-1} b_i 2^i$ | $b_{n-1}b_{n-2}$ ... $b_k b_{k-1}$ ... $b_1 b_0$ | $g_{n-1}g_{n-2}$ ... $g_k g_{k-1}$ ... $g_1 g_0$ |
| ... | ... | ... |
| $2^{n-1}$ | 10 ... 00 00 ... 00 | 110 ... 0 00 ... 00 |
| ... | ... | ... |
| $2^n - 1$ | 11 ... 11 11 ... 11 | 10 ... 00 00 ... 00 |

Figure 15:
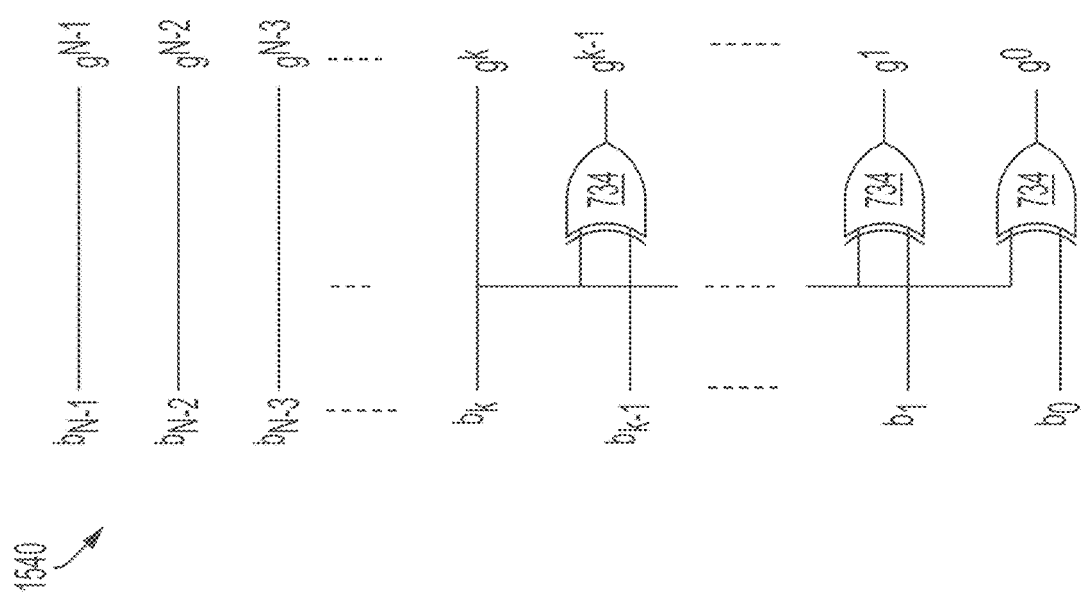
FIG. 15 illustrates another example of gray-coding circuitry, in accordance with certain embodiments described herein.

FIG. 15 illustrates another example of gray-coding circuitry 1540, in accordance with certain embodiments described herein. The gray-coding circuitry 1540 may be used as the gray-coding circuitry 340. In particular, FIG. 15 illustrates gray-coding circuitry 1540 for converting a binary coded value $b_{N-1}b_{N-2}$ ... $b_1b_0$ to a gray coded value $g_{N-1}g_{N-2}$ ... $g_1g_0$ using hybrid gray coding with the k least significant bits using gray coding and the remaining bits using binary coding. The gray-coding circuitry 1540 includes an XOR gate 734 for outputting each of $g_{k-1}$ ... $g_1$, and $g_0$. The XOR gate 734 for outputting a given $g_i$ from $g_{k-1}$ to $g_0$ takes as input $b_k$ and $b_i$. The gray-coding circuitry 1540 outputs $g_i=b_i$ for each of $g_{N-1}$ to $g_k$.

Figure 16:
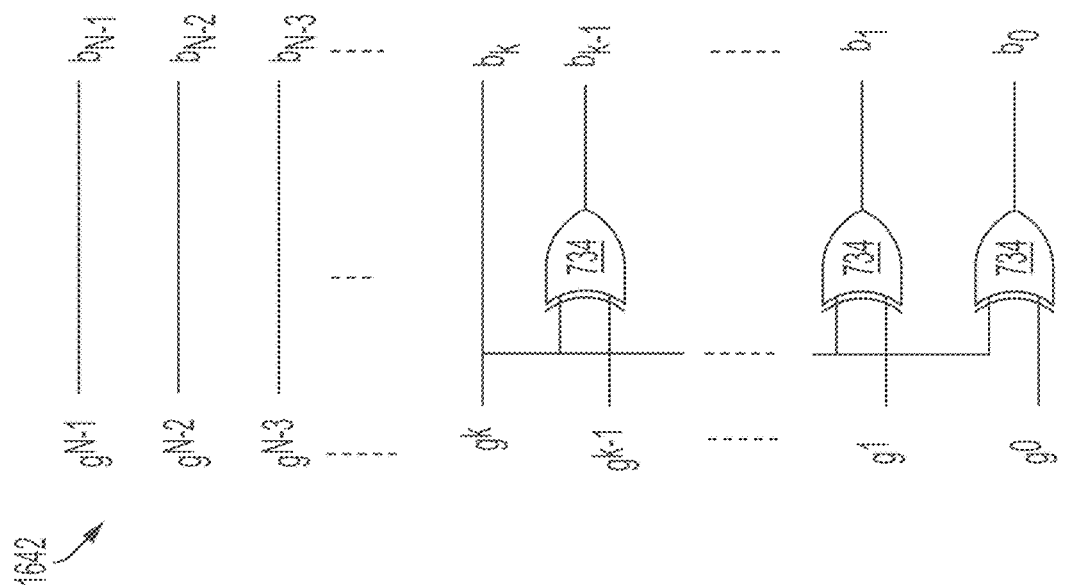
FIG. 16 illustrates another example gray-decoding circuitry, in accordance with certain embodiments described herein.

FIG. 16 illustrates another example of gray-decoding circuitry 1642, in accordance with certain embodiments described herein. The gray-decoding circuitry 1642 may be used as the gray-decoding circuitry 342. In particular, FIG. 16 illustrates gray-decoding circuitry 1642 for converting a gray coded value $g_{N-1}g_{N-2}$ ... $g_1g_0$ that was coded with the gray coding system of the gray-coding circuitry 1640 to a binary coded value $b_{N-1}b_{N-2}$ ... $b_1b_0$. The gray-decoding circuitry for decoding such hybrid gray coding includes an XOR gate 734 for outputting each of $b_{k-1}$ ... $b_1$, and $b_0$. The XOR gate 734 for outputting a given $b_i$ from $b_{k-1}$ to $b_0$ takes as input $g_k$ and $g_i$. The gray-decoding circuitry 1642 outputs $b_i=g_i$ for each of $b_{N-1}$ to $b_k$.

It should be appreciated the gray-coding/decoding systems of FIGS. 15-16 may be helpful for achieving low transition activities in digitally-converted signals with a small signal input. In cases of small signal input, the most-significant bits of a standard binary coded signal may not toggle much anyway, while the least significant bits may. Accordingly, the gray-coding/decoding systems of FIGS. 15-16 may use gray-coding for certain of the least-significant bits but not the remaining bits.

Table 5 illustrates example correspondences between decimal values, binary values, and gray coded values using the gray coding system of the gray-coding circuitry 1540. In Table 5, n bits are used.

TABLE 5

Example correspondences between decimal values, binary values, of gray coded values using the gray coding system of the gray-coding circuitry 1540.

| | | |
|---|---|---|
| 0 | 00 ... 00 00 ... 00 | 00 ... 00 00 ... 00 |
| 1 | 00 ... 00 00 ... 01 | 00 ... 00 00 ... 01 |
| 2 | 00 ... 00 00 ... 10 | 00 ... 00 00 ... 10 |
| ... | ... | ... |
| $2^k - 1$ | 00 ... 00 11 ... 11 | 00 ... 00 11 ... 11 |
| $2^k$ | 00 ... 01 00 ... 00 | 00 ... 01 11 ... 11 |
| $2^k + 1$ | 00 ... 01 00 ... 01 | 00 ... 01 11 ... 10 |
| ... | ... | ... |
| $\Sigma_{i=0}^{n-1} b_i 2^i$ | $b_{n-1}b_{n-2}$ ... $b_k b_{k-1}$ ... $b_1 b_0$ | $g_{n-1}g_{n-2}$ ... $gf_{k-1}$ ... $g_1 g_0$ |
| ... | ... | ... |
| $2^{n-1}$ | 10 ... 00 00 ... 00 | 10 ... 00 00 ... 00 |
| ... | ... | ... |
| $2^n - 1$ | 11 ... 11 11 ... 11 | 11 ... 11 00 ... 00 |

It should be appreciated that ultrasound transducers and any of the circuitry illustrated in FIGS. 3-16 may be integrated on a single semiconductor chip or on multiple semiconductor chips in a stacked configuration.

Figure 18:
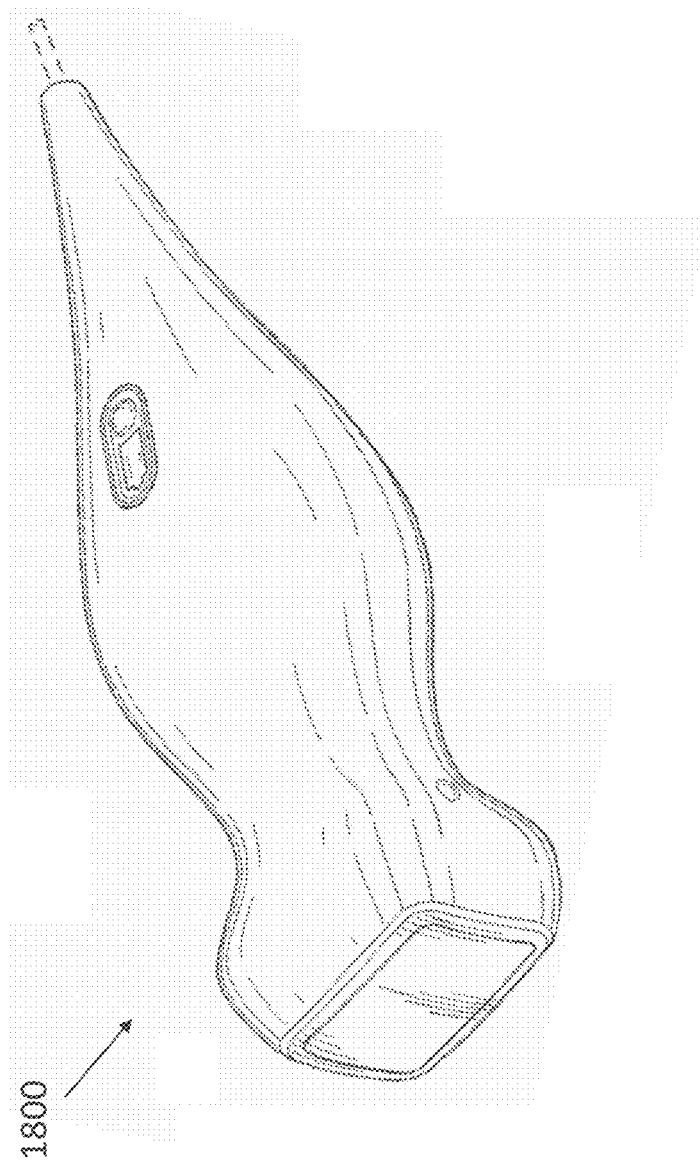
FIG. 18 illustrates an example handheld ultrasound probe, in accordance with certain embodiments described herein.

FIG. 18 illustrates an example handheld ultrasound probe 1800, in accordance with certain embodiments described herein. In some embodiments, an ultrasound-on-chip (e.g., the ultrasound-on-chip 100) including ultrasound transducers and any of the circuitry illustrated in FIGS. 3-16 may be integrated on this ultrasound-on-chip and disposed in the handheld ultrasound probe 1800.

Figure 19:
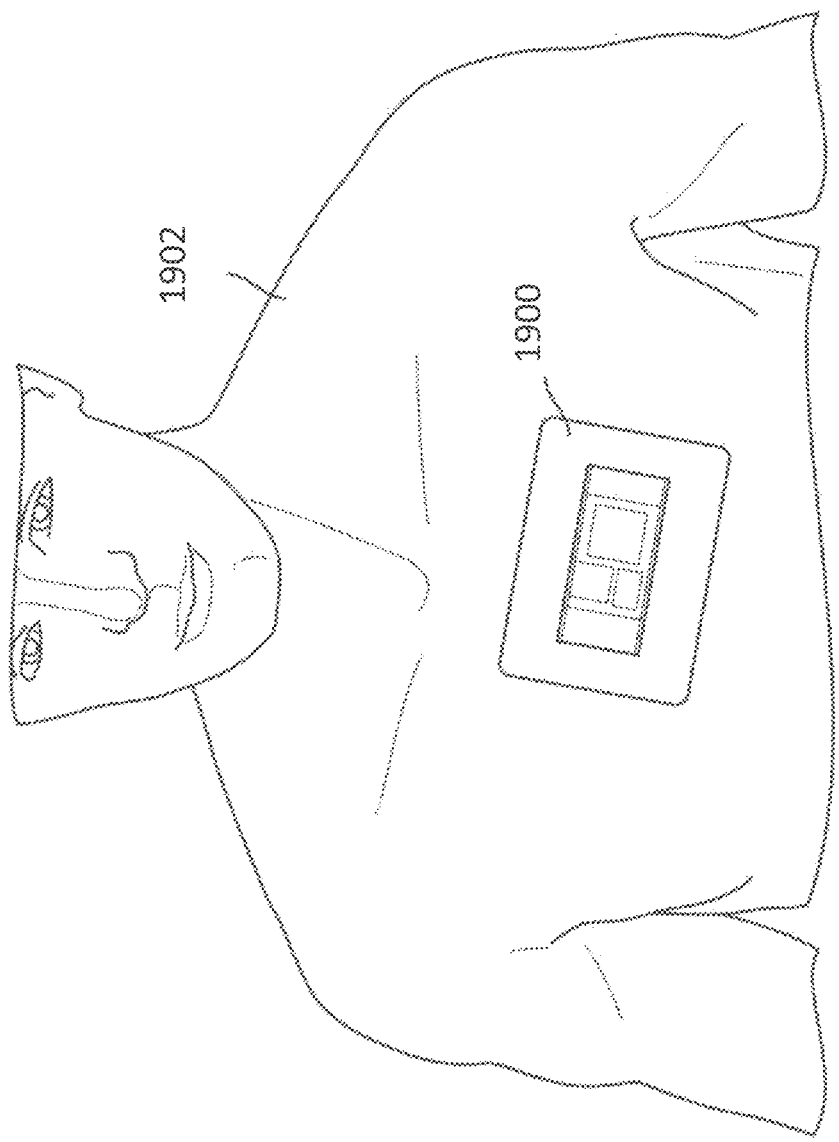
FIG. 19 illustrates an example wearable ultrasound patch, in accordance with certain embodiments described herein.

FIG. 19 illustrates an example wearable ultrasound patch 1900, in accordance with certain embodiments described herein. The wearable ultrasound patch 1900 is coupled to a subject 1902. In some embodiments, an ultrasound-on-chip (e.g., the ultrasound-on-chip 100) including ultrasound transducers and any of the circuitry illustrated in FIGS. 3-16 may be integrated on this ultrasound-on-chip and disposed in the wearable ultrasound patch 1900.

Figure 20:
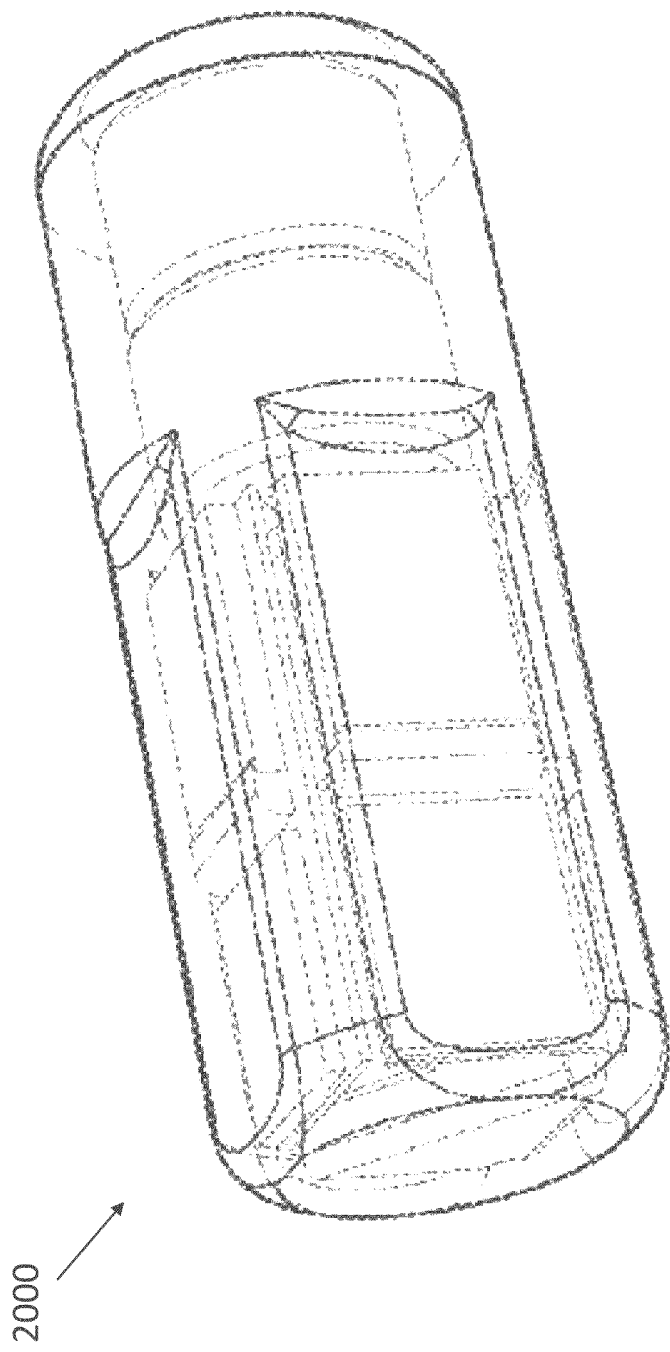
FIG. 20 illustrates an example ingestible ultrasound pill, in accordance with certain embodiments described herein.

FIG. 20 illustrates an example ingestible ultrasound pill 2000, in accordance with certain embodiments described herein. In some embodiments, an ultrasound-on-chip (e.g., the ultrasound-on-chip 100) including ultrasound transducers and any of the circuitry illustrated in FIGS. 3-16 may be integrated on this ultrasound-on-chip and disposed in the ingestible ultrasound pill 2000.

Further description of the handheld ultrasound probe 1800, the wearable ultrasound patch 1900, and the ingestible ultrasound pill 2000 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application).

FIG. 17 illustrates a process 1700 for processing ultrasound signals, in accordance with certain embodiments described herein. The process 1700 is performed by an ultrasound processing unit (UPU) (e.g., a UPU 200) in an ultrasound device. For example, the ultrasound device may be the ultrasound-on-chip device 100.

In act 1702, the UPU receives analog ultrasound signals at an analog portion of the UPU (e.g., at the analog portion 112). Each UPU 200 is a self-contained ultrasound processing unit that forms a sub-array of a complete ultrasound imaging array in a scalable fashion. Each UPU 200 includes an analog portion 112 and a digital portion 110, and may include, for example, any or all of high-voltage pulsers to drive ultrasonic transducers to emit ultrasound; analog and mixed-signal receiver channels to receive and digitize ultrasound echoes; digital processing circuitry to filter, compress, and/or beamform the digital data from each channel; and digital sequencing circuit to control and coordinate different parts of the circuitry to work in sync. The analog portion may be physically separated from the digital portion. The analog portion may include a pulser (e.g., the pulser 318), a switch (e.g., the switch 324), analog processing circuitry (e.g., the analog processing circuitry 326), an ADC (e.g., the ADC 328), and gray-coding circuitry (e.g., the gray-coding circuitry 340, 740, 940, 1140, and/or 1340). The digital portion may include a waveform generator (e.g., the waveform generator 320), gray-decoding circuitry (e.g., the gray-decoding circuitry 342, 842, 1042, 1242, and/or 1442), and digital processing circuitry (e.g., the digital processing circuitry 330).

As described above, in some embodiments the waveform may be configured to provide a waveform to the pulser. The pulser may be configured to output a driving signal corresponding to the received waveform to an ultrasonic transducer (e.g., the ultrasonic transducer 314). The ultrasonic transducer may be configured to emit pulsed ultrasonic signals into a subject, such as a patient, in response to the driving signal received from the pulser. The pulsed ultrasonic signals may be back-scattered from structures in the body, such as blood cells or muscular tissue, to produce echoes that return to the ultrasonic transducer. The ultrasonic transducer may be configured to convert these echoes into electrical signals. Analog processing circuitry may receive the electrical signals representing the received echoes from the ultrasonic transducer. The analog processing circuitry may include, for example, one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, and/or analog averaging circuitry. The process 1700 proceeds from act 1702 to act 1704.

In act 1704, the UPU converts the analog ultrasound signals to standard binary-coded digital ultrasound signals. In some embodiments, the analog processing circuitry may output the analog ultrasound signals to the ADC for conversion to a standard binary-coded digital signal. The ADC may be, for example, a flash ADC, a successive approximation ADC, or a sigma-delta ADC configured to convert analog signals to standard binary-coded digital signals. The process 1700 proceeds from act 1704 to act 1706.

In act 1706, the UPU converts the standard binary-coded digital ultrasound signals to gray-coded digital ultrasound signals. The standard binary-coded digital signals may be outputted to the gray-coding circuitry for conversion from standard binary coding to gray coding. In some embodiments, the gray coding system may be such that every transition from one decimal code to an adjacent decimal code corresponds to a transition from one gray code to another gray code that differs by only a single bit. This may be considered a full gray code system. In some embodiments, the gray coding system may be such that the transition at mid-code (e.g., decimal $2^n-1$ to $2^n$ in an n-bit system) uses a gray code system in that this transition corresponds to a transition from one binary code to another binary code that differs by only a single bit. Other transitions use a standard binary code system in which a transition from one decimal code to an adjacent decimal code may correspond to a transition from one binary code to another binary code that differs by multiple bits. This may be considered a hybrid gray code system with only the most significant bit (MSB) in the gray code system. In some embodiments, the gray coding system may be such that the transitions at each quarter code (e.g., decimal $2^{n-1}-1$ to $2^{n-1}$, $2^n-1$ to $2^n$, and $3*2^{n-2}-1$ to $3*2^{n-2}$ in an n-bit system) use a gray code system in that this transition corresponds to a transition from one gray code to another gray code that differs by only a single bit. Other transitions use a standard binary code system in which a transition from one decimal code to an adjacent decimal code may correspond to a transition from one binary code to another binary code that differs by multiple bits. This may be considered a hybrid gray code system with the most significant bit (MSB) and the second most significant bit (MSB−1) in the gray code system. Further description of gray coding may be found with reference to FIGS. 7, 9, 11, 13, and 15. The process 1700 proceeds from act 1706 to act 1708.

In act 1708, the UPU routes the gray-coded digital ultrasound signals to a digital portion of the UPU. As described above, in embodiments in which the UPU is an ultrasound-on-chip (e.g., the ultrasound-on-chip 100), the ultrasound-on-chip may include multiple ultrasound processing units (UPUs). Multiple UPUs may be tiled along an azimuthal dimension of the ultrasound-on-chip. Ultrasonic transducers may be physically located on top of (i.e., with respect to the depth dimension of the ultrasound-on-chip) the analog portion of each UPU, along the elevational dimension of the ultrasound-on-chip. Due to the arrangement of the ultrasonic transducers on top of the analog portion of each UPU, along the elevational dimension of the ultrasound-on-chip, and due to the tiling of the UPUs along the azimuthal dimension of the ultrasound-on-chip, ultrasonic transducers may be arranged in an array along the azimuthal dimension and elevational dimensions of the ultrasound-on-chip, thus allowing for azimuthal and elevational beamforming of ultrasound signals by the ultrasound-on-chip.

The analog portion of a UPU may include multiple analog front-ends (AFE) (e.g., AFEs 201-208), a block of digital circuitry (e.g., digital circuitry 110), and data buses (e.g., data buses 244A-251A or 244B-251B). The AFEs may be part of the analog portion of each UPU and the digital circuitry may be part of the digital portion of each UPU. The AFEs may be physically arranged in columns, each of the columns including AFEs arranged along the elevational dimension of the ultrasound-on-chip. The digital circuitry may be physically located at one end of the columns along the elevational dimension of the ultrasound-on-chip. Each of the AFEs may include a pulser, a switch, analog processing circuitry, an ADC, and gray-coding circuitry. The digital circuitry may include a waveform generator, gray-decoding circuitry for each AFE, digital processing circuitry for each AFE, multiplexing circuitry, and multiplexed digital processing circuitry. The digital circuitry may be configured to process signals from the AFEs. Thus, the UPU may be configured to route gray-coded digital signals from each of the AFEs to the digital circuitry, which may process the signals from each of the AFEs in a multiplexed fashion. Each of the data buses may be configured to route the gray-coded digital output of an ADC from each of the AFEs to the digital circuitry. Due the physical layout of the UPU, and specifically the arrangement of AFEs along the elevational dimension of the ultrasound-on-chip, certain of the data buses may route digital signals from certain of the AFEs over other AFEs in order to reach the digital circuitry. As described above, digital switching on a data bus passing over analog circuitry in an AFE may introduce noise into analog signals in the AFE. The inventors have recognized that gray coding digital signals on the data buses (in act 1706) may mitigate this effect. The process 1700 proceeds from act 1708 to act 1710.

In act 1710, the UPU converts the gray-coded digital ultrasound signals to standard binary-coded digital ultrasound signals. In some embodiments, the output of the gray-coding circuitry is outputted to gray-decoding circuitry for conversion from gray coding to standard binary coding. Further description of gray decoding may be found with reference to FIGS. 8, 10, 12, 14, and 16. In some embodiments, the output of the gray-decoding circuitry is digitally processed by digital processing circuitry (e.g., digital processing circuitry 330). The digital processing circuitry may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, and/or an output buffer. There may be one block of digital processing circuitry for each AFE. The digital output of the digital processing circuitry for each of the AFEs may be outputted to multiplexing circuitry to be outputted in a multiplexed fashion to multiplexed digital processing circuitry. The multiplexed digital processing circuitry may include, for example, requantization circuitry, waveform removal circuitry, image formation circuitry, and backend processing circuitry. The image formation circuitry may be configured to perform apodization, back projection and/or fast hierarchy back projection, interpolation range migration (e.g., Stolt interpolation) or other Fourier resampling techniques, dynamic focusing techniques, and/or delay and sum techniques, tomographic reconstruction techniques, etc.

In some embodiments, acts 1710 may be absent. For example, digital processing circuitry may be configured to process gray-coded digital signals, thus obviating the need to convert the gray-coded digital signals to standard binary-coded digital signals. In some embodiments, act 1708 may be absent. For example, the gray-coded digital signals may be routed off-chip rather than to the digital portion of the UPU, and off-chip processing may include gray decoding. In some embodiments, instead of acts 1704-1706, circuitry may directly convert the analog ultrasound signals to gray-coded digital ultrasound signals. In some embodiments, act 1702 may be absent, and the UPU may receive ultrasound signals that are already standard binary-coded.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound processing unit (UPU), comprising:
an analog portion configured to receive analog ultrasound signals, the analog portion comprising:
multiple analog front-ends (AFEs) comprising a first AFE and a second AFE, the first AFE of the multiple AFEs comprising:
an analog-to-digital converter (ADC) configured to convert the analog ultrasound signals to standard binary-coded digital ultrasound signals; and
gray-coding circuitry coupled to the ADC and configured to convert the standard binary-coded digital ultrasound signals from the ADC to gray-coded digital ultrasound signals; and
a data bus configured to route the gray-coded digital ultrasound signals from the first AFE to the second AFE;
wherein the data bus passes over the second AFE of the multiple AFEs; and
a digital portion comprising gray-decoding circuitry configured to convert the gray-coded digital ultrasound signals to standard binary-coded digital ultrasound signals.

2. The ultrasound processing unit of claim 1, wherein the digital portion comprises digital processing circuitry.

3. The ultrasound processing unit of claim 1, further comprising multiple data buses each coupled between one of the multiple AFEs and the digital portion.

4. The ultrasound processing unit of claim 1, wherein the analog portion and the digital portion are physically separated.

5. The ultrasound processing unit of claim 1, wherein the analog portion further comprises a pulser, a switch, and analog processing circuitry.

6. The ultrasound processing unit of claim 1, wherein:
an ultrasound-on-chip comprises the ultrasound processing unit; and
the multiple AFEs are arranged along an elevational dimension of the ultrasound-on-chip.

7. The ultrasound processing unit of claim 6, further comprising:
ultrasonic transducers physically located on top of each of the AFEs and arranged along the elevational dimension of the ultrasound-on-chip.

8. The ultrasound processing unit of claim 6, wherein the ultrasound-on-chip comprises an array of ultrasonic transducers along an azimuthal dimension and an elevational dimension of the ultrasound-on-chip.

9. The ultrasound processing unit of claim 1, wherein the gray-coding circuitry is configured to convert the standard binary-coded digital ultrasound signals to hybrid gray-coded digital ultrasound signals.

10. The ultrasound processing unit of claim 9, wherein the gray-decoding circuitry is configured to convert the hybrid gray-coded digital ultrasound signals to the standard binary-coded digital ultrasound signals.

11. An ultrasound processing unit (UPU), comprising:
gray-coding circuitry configured to convert standard binary-coded digital ultrasound signals to full gray-coded digital ultrasound signals,
wherein:
the gray-coding circuitry is configured to convert a standard binary coded value $b_{N-1}b_{N-2} \ldots b_1b_0$ to a gray coded value $g_{N-1}g_{N-2} \ldots g_1g_0$;
the gray-coding circuitry includes an exclusive-or (XOR) gate for outputting each of $g_{N-2}, g_{N-3} \ldots g_1$, and $g_0$, where an XOR gate for outputting a given $g_i$ takes as input $b_{i+1}$ and $b_i$; and
the gray-coding circuitry is configured to output $g_{N-1}=b_{N-1}$.

12. The ultrasound processing unit of claim 11, wherein the gray-coding circuitry is configured to convert the standard binary-coded digital ultrasound signals to the full gray-coded digital ultrasound signals such that every transition from one binary code to an adjacent binary code differs by only a single bit.

13. An ultrasound processing unit (UPU), comprising:
gray-coding circuitry configured to convert standard binary-coded digital ultrasound signals to full gray-coded digital ultrasound signals,
wherein:
the gray-decoding circuitry is configured to convert the full gray-coded digital ultrasound signals to the standard binary-coded digital ultrasound signals;
the gray-decoding circuitry is configured to convert a gray coded value $g_{N-1}g_{N-2} \ldots g_1g_0$ to a standard binary coded value $b_{N-1}b_{N-2} \ldots b_1b_0$;
the gray-decoding circuitry includes an exclusive-or (XOR) gate for outputting each of $b_{N-2}, b_{N-3} \ldots b_1$, and $b_0$, where an XOR gate for outputting a given $b_i$ takes as input $g_i$ and $b_{i+1}$; and
the gray-decoding circuitry is configured to output $b_{N-1}=g_{N-1}$.

14. An ultrasound processing unit (UPU), comprising:
gray-coding circuitry configured to convert standard binary-coded digital ultrasound signals to hybrid gray-coded digital ultrasound signals;
wherein the gray-coding circuitry is configured to convert the standard binary-coded digital ultrasound signals to the hybrid gray-coded digital ultrasound signals such that:
a transition from mid-code to an adjacent binary code uses a gray code system in that
this transition differs by only a single bit; and
other transitions use a standard binary code system.

15. An ultrasound processing unit (UPU), comprising:
gray-coding circuitry configured to convert standard binary-coded digital ultrasound signals to hybrid gray-coded digital ultrasound signals,
wherein:
the gray-coding circuitry is configured to convert a standard binary coded value $b_{N-1}b_{N-2} \ldots b_1b_0$ to a gray coded value $g_{N-1}g_{N-2} \ldots g_1g_0$;
the gray-coding circuitry includes an exclusive-or (XOR) gate for outputting each of $g_{N-2}, g_{N-3} \ldots g_1$, and $g_0$, where an XOR gate for outputting a given $g_i$ takes as input $b_{N-1}$ and $b_i$; and
the gray-coding circuitry is configured to output $g_{N-1}=b_{N-1}$.

16. An ultrasound processing unit (UPU), comprising:
gray-coding circuitry configured to convert standard binary-coded digital ultrasound signals to hybrid gray-coded digital ultrasound signals; and
gray-decoding circuitry,
wherein:
the gray-coding circuitry is configured to convert the standard binary-coded digital ultrasound signals to hybrid gray-coded digital ultrasound signals;
the gray-decoding circuitry is configured to convert the hybrid gray-coded digital ultrasound signals to the standard binary-coded digital ultrasound signals;
the gray-decoding circuitry is configured to convert a gray coded value $g_{N-1}g_{N-2} \ldots g_1 g_0$ to a standard binary coded value $b_{N-1}b_{N-2} \ldots b_1 b_0$;
the gray-decoding circuitry includes an exclusive-or (XOR) gate for outputting each of $b_{N-2}, b_{N-3} \ldots b_1$, and $b_0$, where an XOR gate for outputting a given $b_i$ takes as input $g_i$, and $g_{N-1}$; and
the gray-decoding circuitry outputs $b_{N-1}=g_{N-1}$.

* * * * *